United States Patent
Mann et al.

(10) Patent No.: US 8,574,849 B2
(45) Date of Patent: Nov. 5, 2013

(54) METHODS OF DETECTION OF FACTOR XIA AND TISSUE FACTOR

(75) Inventors: Kenneth G. Mann, Grand Isle, VT (US); Saulius Butenas, South Burlington, VT (US); Anetta Undas, Krakow (PL)

(73) Assignee: The University of Vermont and State Agriculture College, Burlington, VT (US)

( * ) Notice: Subject to any disclaimer, the term of this patent is extended or adjusted under 35 U.S.C. 154(b) by 217 days.

(21) Appl. No.: 12/681,232

(22) PCT Filed: Oct. 3, 2008

(86) PCT No.: PCT/US2008/078712
§ 371 (c)(1),
(2), (4) Date: Jun. 10, 2010

(87) PCT Pub. No.: WO2009/046274
PCT Pub. Date: Apr. 9, 2009

(65) Prior Publication Data
US 2010/0261198 A1  Oct. 14, 2010

Related U.S. Application Data

(60) Provisional application No. 60/997,518, filed on Oct. 3, 2007, provisional application No. 60/986,349, filed on Nov. 8, 2007.

(51) Int. Cl.
*G01N 33/53* (2006.01)
(52) U.S. Cl.
USPC ............................................. 435/7.1; 435/7.2
(58) Field of Classification Search
None
See application file for complete search history.

(56) References Cited

U.S. PATENT DOCUMENTS 5,750,358 A    5/1998  Morrissey
2002/0042144 A1*  4/2002  Mann et al. ............... 436/69

FOREIGN PATENT DOCUMENTS

| JP | 07134129 A | 5/1995 |
|---|---|---|
| KR | 10-2002-0042622 A | 6/2002 |
| WO | 01/07070 A1 | 2/2001 |

OTHER PUBLICATIONS

Scandura et al. (Biochemistry 1999 vol. 36, p. 412-420).*
P.G. Board et al., "The use of fluorogeneic peptide substrates for the detection of coagulation factors II and X after electrophoresis", Ann. Hum. Genet., vol. 46, pp. 293-298 (1982).
S. Butenas et al., "Factor XIa and tissue factor activity in patients with coronary artery disease." In Thromb. Haemost. vol. 99:142-149 (Published online Dec. 5, 2007).
Scott et al., "Inactivation of Factor XIa by Plasma Protease Inhibitors." In J. Clin. Invest. @ The American Society for Clinical Investigation, Inc. vol. 69:844-852(Apr. 1982).
Wuillemin et al., "Inactivation of Factor XIa in Human Plasma Assessed by Measuring Factor XIa-Protease Inhibitor Complexes: Major Role for C1-Inhibitor." In Blood, vol. 85, No. 6:1517-1526(Mar. 15, 1995).
Minnema et al., "Activation of Clotting Factors XI and IX in Patients With Acute Myocardial Infarction." In Arterioscler Thromb Vasc Biol. vol. 20:2489-2493(Nov. 2000).
International Search Report for PCT/US2008/078712 dated Feb. 26, 2009.

\* cited by examiner

*Primary Examiner* — Jacob Cheu
(74) *Attorney, Agent, or Firm* — Edwards Wildman Palmer LLP; David G. Conlin; Lisa Swiszcz

(57) ABSTRACT

The invention provides compositions and methods for the detection of Factor XIa or Tissue Factor (TF) activity in a sample using an antibody based clotting time prolongation assay. The invention provides methods for detection of FXIa or TF activity in a sample using a fluorogenic substrate. Further provided herein is a correlation between elevated levels of FXIa and/or TF with inflammation, acute coronary syndrome (ACS), myocardial infarction, coronary artery disease (CAD), heart failure, aortic stenosis, stroke, or transient ischemic attack. The frequency of FXIa and TF activity was substantially lower in individuals with stable coronary artery disease and no history of myocardial infarction. No FXIa or TF activity was observed in healthy individuals.

4 Claims, 7 Drawing Sheets

METHODS OF DETECTION OF FACTOR XIA AND TISSUE FACTOR

CROSS-REFERENCE TO RELATED APPLICATIONS

The application is a National Phase entry of PCT Application PCT/US2008/078712, filed on Oct. 3, 2008 which claims priority to U.S. Provisional Patent Applications 60/997,518 filed on Oct. 3, 2007 and 60/986,349 filed Nov. 8, 2007. All of the applications are incorporated herein by reference in their entirety.

STATEMENT AS TO FEDERALLY SUPPORTED RESEARCH

This invention was made with Government support under Grant No. PO1 HL46703 awarded by the National Institutes of Health. The Government has certain rights in the invention.

BACKGROUND

Inflammatory processes and enhanced procoagulant activity are closely related to the development of atherosclerotic plaques. Plaque disruption and subsequent thrombosis are the leading cause of acute coronary syndromes (ACS), including unstable angina, acute myocardial infarction and sudden death. Pro-inflammatory cytokines cause a disruption of normal function of the arterial endothelium leading to the up-regulation of adhesion molecules, which contribute to plaque growth. Circulating levels of pro-inflammatory cytokines are increased in ACS patients and are predictors of the onset and outcome of coronary artery disease (CAD). One of the functions of cytokines is stimulation of tissue factor (TF) expression, which is a potent initiator of the coagulation cascade and plays a major role in plaque thrombogenicity. It has been also suggested that thrombin-driven and contact pathway-independent activation of factor (F) XI can play a role in cardiovascular disease. For example, Minnema et al. (*Arterioscler Thromb Vasc Biol* 2000; 20(11):2489-2493) reported that 24% of patients with acute myocardial infarction and 8% with unstable angina pectoris had evidence of FXIa presentation in their plasma Minnema's assay was based upon the immunochemical detection of FXIa in complex with C1 inhibitor; one of the numerous serine protease inhibitors present in plasma, suggesting that potentially only a fraction of FXIa present in plasma was detected by this procedure.

The detection of FXIa in plasma is complicated by controversies related to the efficiency of various plasma protease inhibitors towards FXIa. Wuillemin and coworkers suggest that 47% of FXIa added to plasma forms a complex with C1 inhibitor (Wuillemin W A, et al., *Blood* 1995; 85(6):1517-1526), whereas Scott et al. report that only 8% of FXIa is involved in the complex formation with this inhibitor. (Scott C F, et al., *J Clin Invest* 1982; 69(4): 844-852)

SUMMARY OF THE INVENTION

The present invention provides a method for the detection of Factor (F) XIa activity or Tissue Factor (TF) activity in a test sample. The present invention also provides methods for the diagnosis of cardiovascular disease that feature methods of detecting FXIa activity and/or TF activity. The present invention further provides methods for the stratification of patients with stable coronary artery disease (CAD) by identifying those with increased procoagulant activity correlated with increased propensity for acute coronary syndrome (ACS) that feature methods of detecting FXIa activity and/or TF activity.

The invention includes methods of detecting FXIa activity in a test sample by sequentially contacting the test sample with a FXIa specific antibody; contacting the test sample with $Ca^{++}$ and a phospholipid surface; and determining clotting time of the test sample. The clotting time for the test sample is compared to the clotting time of a control sample from the same subject or source not treated with an FXIa specific antibody, prior to contacting the sample with $Ca^{++}$ and a phospholipid surface. The prolongation of clotting time of the test sample as compared to the control sample is indicative of the presence of FXIa in the test sample. The sample can be obtained from a subject, particularly a subject suspected of or known to be suffering from inflammation, coronary artery disease, and/or acute coronary syndrome. A prolongation of clotting time is indicative of inflammation, acute coronary syndrome, and/or coronary artery disease.

The invention includes methods of detecting FXIa activity in a test sample by sequentially contacting the test sample with a fluorogenic substrate such as 6,1-D-LPR-propylami-nonaphthalenesulfonamide, and monitoring the cleavage of the substrate over time wherein cleavage is indicative of the presence of FXIa activity. Similarly chromogenic substrates can be used.

The invention includes methods for assisting in the diagnosis and/or stratification of cardiovascular disease in subjects, particularly for diagnosis of acute coronary syndrome, myocardial infarction, heart failure, and stroke, and for stratification of subjects suspected of having or having acute coronary syndrome, and stable coronary artery disease with an elevated risk for ACS; and stratification of subjects for stroke, acute stroke, and transient ischemic attack, all by detection of an elevated level of FXIa activity. The elevated activity level can be detected by any method that specifically detects the presence of FXIa in a sample. The elevated level can be relative to no activity in a normal (i.e., no cardiovascular disease) subject. The methods can be used in combination with the detection of other signs or symptoms of a particular disease or condition for the diagnosis and/or stratification of the disease or condition.

The methods detection of elevated FXIa activity in a subject include obtaining a test sample, preferably a blood, plasma or serum sample, from a subject suffering from or suspected of suffering from cardiovascular disease and contacting the test sample with a calcium chelator and an inhibitor of the contact pathway of inhibition that does not inhibit FXIa, such as seed trypsin inhibitors (e.g., corn, barley, pumpkin, cashewnut), specific kallikrein inhibitors (e.g., aprotinin), HMW kininogen inhibitors (e.g., elastase treatment), FXIIa specific inhibitors (e.g., antibodies). A portion of the treated sample then is contacted with an FXIa specific antibody under conditions to permit binding of the antibody to FXIa. The sample is subsequently contacted with $Ca^{++}$ and a phospholipid surface; and clotting time of the sample portion is determined A second portion of the chelator-contact pathway inhibitor treated sample is contacted with $Ca^{++}$ and a phospholipid surface; and clotting time of the second sample portion is determined. The clotting time of the antibody treated first portion is compared to the clotting time of the second portion. A prolongation of clotting time in the first portion is indicative of the presence of FXIa in the sample that is correlated with cardiovascular disease, particularly with acute coronary syndrome, stroke, transient ischemic attack, heart failure and aortic stenosis and/or elevated risk for acute coronary syndrome with stable coronary artery disease.

Alternatively, methods of detecting FXIa activity in a subject sample include sequentially contacting the test sample treated sequentially with chelator-contact pathway inhibitor that does not inhibit FXIa; $Ca^{++}$; a fluorogenic substrate such as 6,1-D-LPR-propylaminonaphthalenesulfonamide; and monitoring the cleavage of the substrate over time wherein cleavage is indicative of the presence of FXIa activity.

The invention includes kits for the detection of FXIa in a sample. The kits include a FXIa specific antibody and at least one of a calcium chelator, a solution containing $Ca^{++}$, phospholipids, and a control sample such as FXIa, particularly recombinant FXIa, or any combination thereof, with appropriate packaging material. The kits can also include a fluorogenic substrate such as 6,1-D-LPR-propylaminonaphthalenesulfonamide and a control sample such as FXIa, particularly recombinant FXIa, with appropriate packing material. Kits can further include reagents or instructions for detection of TF by methods disclosed herein or other previously known methods.

The invention includes methods of detecting Tissue Factor (TF) in a test sample by sequentially contacting the test sample with a TF specific antibody; contacting the test sample with $Ca^{++}$ and a phospholipid surface; and determining clotting time of the test sample. The clotting time for the test sample is compared to the clotting time of a control sample obtained from the same subject or source not treated with a TF specific antibody, prior to contacting the sample with $Ca^{++}$ and a phospholipid surface. The prolongation of clotting time of the antibody treated test sample as compared to the control sample is indicative of the presence of TF in the test sample. The sample can be obtained from a subject, particularly a subject suspected of or known to be suffering from inflammation and cardiovascular disease, particularly coronary artery disease, stroke, transient ischemic attack, heart failure, aortic stenosis and/or acute coronary syndrome. A prolongation of clotting time in the antibody treated sample is indicative of inflammation and/or cardiovascular disease. Although TF is not present in many subjects with cardiovascular disease, it was not found in any subjects without cardiovascular disease. Therefore, it is a positive indicator of disease.

The invention includes methods of detecting TF activity in a test sample by sequentially contacting the test sample with a fluorogenic substrate such as D-FPR-ANSNC$_6$H$_{11}$ or D-FPR-ANSNC$_4$H$_9$ and monitoring the cleavage of the substrate over time wherein cleavage is indicative of the presence of TF activity. Similarly chromogenic substrates can be used.

The invention includes methods for assisting in the diagnosis and/or stratification of cardiovascular disease in subjects, particularly in subjects with heart failure, acute coronary syndrome, and stable coronary artery disease with an elevated risk for ACS by detection of an elevated level of TF activity. The elevated level can be detected by any method that specifically detects the presence of TF in a sample. The methods can be used in combination with the detection of other signs or symptoms of a particular disease or condition for the diagnosis and/or stratification of the disease or condition.

The methods of detection of elevated TF activity include obtaining a test sample, preferably a blood or plasma sample, from a subject suffering from or suspected of suffering from cardiovascular disease, particularly acute coronary syndrome and/or coronary artery disease, and contacting the test sample with a calcium chelator and an inhibitor of the coagulation contact pathway that does not inhibit TF, such as seed trypsin inhibitors (e.g., corn, barley, pumpkin, cashewnut), specific kallikrein inhibitors (e.g., aprotinin), and HMW kininogen inhibitors (e.g., elastase treatment), and FXIIa specific inhibitors (e.g., antibodies). A portion of the treated sample then is contacted with a TF specific antibody under conditions to permit binding of the antibody to TF. The antibody treated sample is subsequently contacted with $Ca^{++}$ and a phospholipid surface; and clotting time of the sample portion is determined. A second portion of the chelator-contact pathway inhibitor treated sample is contacted with $Ca^{++}$ and a phospholipid surface; and clotting time of the second sample portion is determined. The clotting time of the first antibody treated portion is compared to the clotting time of the second portion. A prolongation of clotting time in the first portion relative to the second portion is indicative of the presence of TF in the sample which is correlated with cardiovascular disease in the subject.

Alternatively, methods of detecting TF activity in a test sample include sequentially contacting the test sample with a chelator-contact pathway inhibitor that does not inhibit TF and subsequently with $Ca^{++}$ and a fluorogenic substrate such as D-FPR-ANSNC$_6$H$_{11}$ or D-FPR-ANSNC$_4$H$_9$, and monitoring the cleavage of the substrate over time wherein cleavage is indicative of the presence of TF activity. Similarly chromogenic substrates can be used.

The invention includes kits for the detection of TF in a sample. The kits include a TF specific antibody and at least one of a calcium chelator, an inhibitor of the coagulation contact pathway that does not inhibit TF, a solution containing $Ca^{++}$, phospholipids, and a control sample such as TF, particularly recombinant TF, or any combination thereof, with appropriate packaging material. The kits can also include a fluorogenic substrate such as D-FPR-ANSNC$_6$H$_{11}$ and D-FPR-ANSNC$_4$H$_9$, and a control sample such as TF, particularly recombinant TF, with appropriate packing material. Kits can further include reagents or instructions for detection of FXIa by methods disclosed herein or other previously known methods. Similarly chromogenic substrates can be used.

DEFINITIONS

"Acute coronary syndrome" (ACS) as used herein is a set of signs and symptoms, usually a combination of chest pain and other features related to decreased blood flow to the heart (cardiac ischemia). The most common cause for this is the disruption of atherosclerotic plaque in an epicardial coronary artery. The subtypes of acute coronary syndrome include unstable angina (UA, not associated with heart muscle damage), and two forms of myocardial infarction (heart attack), in which heart muscle is damaged. These types are named according to the appearance of the electrocardiogram (ECG/EKG) as non-ST segment elevation myocardial infarction (NSTEMI) and ST segment elevation myocardial infarction (STEMI).

"Aortic stenosis" as used herein is the abnormal narrowing of the aorta resulting in decreased blood flow through the artery. Aortic stenosis, and vascular stenosis, can be caused, for example, by atherosclerosis, ischemia, infection, and inflammation.

"Calcium ion" or "$Ca^{++}$" is understood herein as a divalent cation of calcium. Calcium ion is typically provided to a sample in the form of $CaCl_2$ as a solution. However, calcium ion can be provided using any of a number of other calcium compounds.

A "calcium chelator" as used herein is a sequestering agent that binds or complexes with calcium ion making it chemically inert, effectively removing from a sample. Calcium chelators include, but are not limited to citrate, preferably sodium citrate, ethylene glycol tetraacetic acid (EGTA), and ethylenediamine tetraacetic acid (EDTA).

"Cardiovascular disease" as used herein refers to a large number of diseases class of diseases that involve the heart or blood vessels (arteries and veins). Cardiovascular disease includes, but is not limited to, atherosclerosis, acute coronary syndrome, coronary artery disease, heart failure, vascular stenosis, particularly aortic stenosis, stroke, myocardial infarction, aneurysm, angina, myocarditis, valve disease, coronary artery disease, dilated cardiomyopathy, endocarditis, hypertension, heart failure, hypertrophic cardiomyopathy, myocardial infarction, transient ischemic attack (TIA), and venous thromboembolism.

A "contact pathway coagulation inhibitor" that does not inhibit FXIa or TF as used herein is a compound that prevents coagulation of the contact pathway of coagulation that does not inhibit FXIa or TF, such as seed trypsin inhibitors (e.g., corn, barley, pumpkin, cashew nut, paprika, watermelon seed); and FXIIa, kallikrein, and HMW kininogen specific inhibitor antibodies. In a preferred embodiment, the inhibitor is a seed trypsin inhibitor particularly corn trypsin inhibitor. The seed trypsin inhibitor can be isolated from the seeds or expressed as a recombinant protein. For examples of seed inhibitors, see e.g., Fagbemi et al., 2005 *Pakistani J. Nutr.* 4:250-256; El-Adawy and Taha, 2001 *J. Agric. Food Chem.* 49:1253-1259; and Alfonso-Rubi et al, 2003 *Transgenic Res.* 12:23-31 (all incorporated herein by reference).

"Coronary artery disease" (CAD), also known as coronary heart disease (CHD), ischemic heart disease, and atherosclerotic heart disease is characterized by the accumulation of atherosclerotic plaques within the walls of the arteries that supply the myocardium. While the symptoms and signs of coronary heart disease are noted in the advanced state of disease, most individuals with coronary heart disease show no evidence of disease for decades as the disease progresses before the first onset of symptoms, such as myocardial infarction (MI). Unstable CAD can lead to ACS.

"Coronary artery bypass graft", commonly known as CABG (pronounced "cabbage") or heart bypass or bypass surgery is a surgical procedure performed to relieve angina and reduce the risk of death from coronary artery disease. Arteries or veins from elsewhere in the patient's body are grafted to the coronary arteries to bypass atherosclerotic narrowings and improve the blood supply to the coronary circulation supplying the myocardium (heart muscle).

As used herein, "detecting", "detection" and the like are understood that an assay was performed for a specific analyte, such as FXIa or TF, in a sample. The amount of analyte detected in the sample can be none or below the level of detection of the assay.

By "diagnosis", "diagnosing", and the like is meant the art or act of identifying a disease from its signs and symptoms. Diagnosis can include the detection of a number of signs or symptoms, including detection of the presence or absence of specific proteins in a subject sample, for the diagnosis of a specific disease or condition of a subject. Each sign or symptom of the disease or condition in addition to the medical history of the subject is used for the purpose of diagnosis and contributes to the final diagnosis. No single sign or symptom need be definitive for the diagnosis of a disease or condition alone. As used herein, having a disease or condition can include a subject that is suffering from a specific disease at the moment that the sample is obtained, e.g., during the heart attack, stroke or other ischemic event, or a subject that has suffered from a specific disease or disorder, within the past day, week, month, months, or longer in the past.

A "Factor XIa (FXIa) specific antibody" refers to an immunoglobulin protein that is capable of binding specifically and preferentially to FXI/FXIa and inhibit the activity of FXIa by at least 30%, at least 40%, at least 50%, at least 60%, least 70%, at least 80%, at least 90%, at least 95%, at least 99%, at least 100%. Methods to determine decreased activity are well known to those skilled in the art (e.g., by measuring an increase in coagulation time). Preferably a FXIa specific antibody binds FXIa with an affinity of at least $10^{-6}$/M, $10^{-7}$/M, $10^{-8}$/M, $10^{-9}$/M, $10^{-10}$/M, $10^{-11}$/M, or $10^{-12}$/M under specified conditions of the instant invention. Methods to measure affinity are well known to those skilled in the art.

A FXIa specific antibody is preferably a monoclonal antibody, scFv, or other monospecific antibody or antibody fragment. A FXIa antibody can be a polyclonal antibody. Antibody includes any portion of an antibody that retains the ability to bind to FXIa specifically. Examples of antibody fragments preferably include, but are not limited to, Fab, Fab', and F(ab')$_2$, Fd, single-chain Fvs (scFv), single-chain antibodies, disulfide-linked Fvs (sdFv) and fragments comprising either a $V_L$ or $V_H$ domain Epitope-binding fragments, including single-chain antibodies, may comprise the variable region(s) alone or in combination with the entirety or a portion of the following: hinge region, $C^H_1$, $C^H_2$, and $C^H_3$ domains. As used herein, the FXIa antibody is contacted with a sample suspected of containing FXIa under conditions to permit binding (e.g., physiological salt and pH at 25-37° C.). Conditions that permit antibody-antigen binding will vary somewhat depending on the antibody used. Methods to select conditions to permit binding are well within the ability of those skilled in the art. FXIa specific antibodies are commercially available, for example from Heamatologic Technologies, Inc.

As used herein, "fluorogenic substrate" is understood as specific protease substrate for FXIa and/or TF activity. Upon cleavage of the substrate, it undergoes a shift in fluorescence to allow for detection of formation of the cleavage product. Selection of a specific fluorogenic substrate is within the ability of those skilled in the art. Exemplary fluorogenic substrates are taught, for example, in U.S. Pat. Nos. 5,399,487 and 6,566,493, both incorporated herein by reference, and are available, for example from Haemtologic Technologies, Inc, (Essex Junction, Vt.). A fluorogenic substrate for any protease of interest can be identified, for example, but the use of methods such as those taught in the Examples of the U.S. Pat. No. 5,399,487 (incorporated herein by reference). The amount and kinetics of cleavage can be modulated by increasing or decreasing the amount of enzyme and the amount of substrate and other parameters such as temperature and pH. Methods to select appropriate concentrations of enzyme and substrate are well known to those skilled in the art. Chromogenic substrates can also be used in the methods of the invention with detection of the formation of the product at an appropriate wavelength.

As used herein, "heart failure" is understood as Heart failure is a cardiac condition, that occurs when a problem with the structure or function of the heart impairs its ability to supply sufficient blood flow to meet the body's needs. Heart failure should not be confused with cardiac arrest. It can cause a large variety of symptoms (chiefly shortness of breath and ankle swelling) but some patients can be completely symptom free. Heart failure is often undiagnosed due to a lack of a universally agreed definition and challenges in definitive diagnosis, particularly in early stage.

As used herein, "increased relative to a normal reference sample" is understood as having a level of FXIa or TF at a level that is statistically greater than a sample from a normal subject, preferably a pooled sample from multiple normal subjects under standard reaction conditions, such as those provided herein and references cited herein. Depending on the method used for detection the amount and measurement of the increase can vary. For example, an increase in the rate or amount of cleavage of a fluorogenic substrate will depend on the exact reaction conditions. Determination of statistical significance is within the ability of those skilled in the art. Significant increases in clotting time are defined herein.

As used herein, "isolated" or "purified" when used in reference to a polypeptide means that a naturally polypeptide or protein has been removed from its normal physiological environment (e.g., protein isolated from plasma or tissue) or is synthesized in a non-natural environment (e.g., artificially synthesized in a heterologous system). Thus, an "isolated" or "purified" polypeptide can be in a cell-free solution or placed in a different cellular environment. The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide.

As used herein, "kits" are understood to contain at least the non-standard laboratory reagents for use in the methods of the invention, such as the specific antibody or antibodies required for the use in the method and the protein at a known amount or concentration to act as a positive control in the method of the invention. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

If desired compositions of the invention or combinations thereof are provided together with instructions for testing a sample from a subject having or at risk of developing a cardiac disease or disorder. The instructions will generally include information about the use of the compounds for the diagnosis or stratification of a subject having or suspected of having a cardiac disease or disorder such as CAD and/or ACS. In other embodiments, the instructions include at least one of the following: description of the compound or combination of compounds; precautions; warnings; indications; counter-indications; and/or references. The instructions may be printed directly on the container (when present), or as a label applied to the container, or as a separate sheet, pamphlet, card, or folder supplied in or with the container.

"Obtaining" is understood herein as manufacturing, purchasing, or otherwise obtaining.

A "phospholipid surface" as understood herein is a phospholipid bilayer, vesicle, or micelle having an acidic phospholipid component such as phosphatidylserine (PS) derivatives, capable of promoting clotting of plasma or blood by FXIa. The phospholipid surface can be generated using purified phospholipids as previously described (e.g., see Higgins and Mann, 1983, incorporated herein by reference). Alternatively, a phospholipid surface can be generated using cell membranes or other partially purified sources of phospholipids. Phosphatidylcholine (PC), phosphatidylseine (PS), phosphatidylethanolamine (PE), and phosphatidylglycerol (PG) can be purchased from Avanti Polar Lipids, Alabaster, Ala. Phospholipid vesicles can be composed of either 75:25 PC:PS or a blend of PC:PS:PG:PE and perform well in in vitro coagulation assays. Vesicles can be formed utilizing a process involving solubilizing the lipid blend in the presence of zwiterionic detergent that is subsequently removed chromatographically.

The method is scaleable and is particularly well suited to large-scale manufacturing. Phospholipid vesicles are prepared by a previously reported sonication method described in Barenholz et al. (A simple method for the preparation of homogeneous phospholipid vesicles. *Biochemistry*. 1977; 16:2806-2810, incorporated herein by reference).

As used herein, "plurality" is understood to mean more than one. For example, a plurality refers to at least two, three, four, five, or more.

As used herein a test or assay that is a "positive predictor" or an assay that has "positive predictive value" is understood as a test or assay in which a positive result for the test, e.g., the presence of a specific factor in a patient sample, e.g., the presence of FXIa in the serum is strongly predictive of the presence of a disease or condition. However, the absence of a positive result from the test is not necessarily indicative of the absence of a disease or condition. In an embodiment, the positive result indicates with at least 70% accuracy, 80% accuracy, 85% accuracy, 90% accuracy, 95% accuracy, or more that the subject is suffering from a disease or condition correlated with a positive result in the assay or test. In an embodiment, the positive result is present in at least 50%, 60%, 70%, 80%, 90% or more of the subjects suffering from a disease or condition.

A "prolongation in clotting time" or "increase in clotting time" is understood herein as a clotting time that increased relative to a reference. The increase is by at least 10%, at least 25%, at least 50%, at least 75%, at least 100%, at least 150%, at least 200%. Clotting time is typically monitored over about 3000 seconds at 37° C. In normal samples, clotting does not occur within the time of the experiment. In order to calculate an increase in clotting time, clotting is arbitrarily considered to have occurred at 3000 seconds or at the end of the time of assay, whichever is longer if no clotting has occurred during the time of the assay. Clotting time can be measured using any of a number of commercially available apparatuses or assays including, but not limited to an ST8 instrument from Diagnostica Stago, a Hemochron® instrument from ITC (Edison, N.J.), and a thrombelastograph (TEG) ecarin clotting time (ECT) assay.

A "propensity to develop or suffer from" is a greater likelihood of developing and/or suffering from a disease or condition. A greater likelihood is at least about 50% more likely, at least about 75% more likely, at least about 100% more likely, at least about 150% more likely, at least about 200% more likely.

"Providing," refers to obtaining, by for example, buying or making a reagent, material, or device. The material provided may be made by any known or later developed biochemical or other technique.

A "sample" as used herein refers to a biological material that is isolated from its natural environment and is suspected of, or possibly containing an analyte, such as FXIa or TF. Most commonly a sample is blood or plasma. A sample can also be a partially purified fraction of a tissue or bodily fluid. A reference sample can be a "normal" sample, typically a pooled normal sample from a number of donors not having the disease or condition which should not contain detectable FXIa or TF. A sample can contain a known amount of FXIa or TF as a reference sample. A sample, particularly a test sample, can contain an unknown amount of FXIa or TF as a test sample.

"Stratification" as used herein is a ranking, either numerical or relative, of the chance of a subject progressing from CAD, either stable or unstable, to ACS based on the presence of FXIA, TF, and/or elevated levels of inflammatory markers in the blood. A subject with no detectable FXIa, TF, and/or low levels of inflammatory markers (i.e., the same as or only slightly elevated, for example less than about 10%, less than about 20%, less than about 30% higher than a subject without cardiovascular disease) has less chance of progressing from CAD to ACS as compared to a subject who has elevated levels of FXIa, TF, and/or elevated levels of inflammatory markers (e.g., at least about 70%, at least about 80%, at least about 100%, at least about 200% higher than a subject without cardiovascular disease). It is understood that the specific amount of variation in the level of FXIA, TF, or a particular inflammatory marker in a subject compared to control to make a subject considered to be "higher risk" will depend on the compound considered. Stratification of subjects can be used for the purpose of diagnosis and/or selection of an appropriate therapeutic regimen for treatment of a subject with cardiovascular disease.

As used herein, "stroke" is understood as the rapidly developing loss of brain functions due to a disturbance in the blood vessels supplying blood to the brain. This can be due to ischemia caused, for example, by thrombosis or embolism or due to a hemorrhage.

A "subject" as used herein refers to living organisms. In certain embodiments, the living organism is an animal. In certain preferred embodiments, the subject is a mammal. In certain embodiments, the subject is a domesticated mammal. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of characteristics of the disease, condition, or syndrome such that a competent individual would diagnose or suspect that the subject was suffering from the disease, condition, or syndrome. Methods for identification of subjects suffering from or suspected of suffering from conditions such as ACS or CAD is within the ability of those in the art. Subjects suffering from and suspected of suffering from a specific disease, condition, or syndrome are not necessarily two distinct groups.

A "Tissue Factor (TF) specific antibody" refers to an immunoglobulin protein that is capable of binding specifically and preferentially to TF and inhibit the activity of TF by at least 30%, at least 40%, at least 50%, at least 60%, least 70%, at least 80%, at least 90%, at least 95%, at least 99%, at least 100%. Methods to determine decreased activity are well known to those skilled in the art (e.g., by measuring an increase in coagulation time). Preferably a TF specific antibody binds TF with an affinity of at least $10^{-6}$/M, $10^{-7}$/M, $10^{-8}$/M, $10^{-9}$/M, $10^{-10}$/M, $10^{-11}$/M, or $10^{-12}$/M under specified conditions of the instant invention. Methods to measure affinity are well known to those skilled in the art.

A TF specific antibody is preferably a monoclonal antibody, scFv, or other monospecific antibody or antibody fragment. A TF antibody can be a polyclonal antibody. Antibody includes any portion of an antibody that retains the ability to bind to TF specifically. Examples of antibody fragments preferably include, but are not limited to, Fab, Fab', and F(ab')$_2$, Fd, single-chain Fvs (scFv), single-chain antibodies, disulfide-linked Fvs (sdFv) and fragments comprising either a $V_L$, $V_H$, or $V_{HH}$ domain. Epitope-binding fragments, including single-chain antibodies, may comprise the variable region(s) alone or in combination with the entirety or a portion of the following: hinge region, $C^H_1$, $C^H_2$, and $C^H_3$ domains. As used herein, the TF antibody is contacted with a sample suspected of containing TF under conditions to permit binding (e.g., physiological salt and pH at 25-37° C.). Conditions that permit antibody-antigen binding will vary somewhat depending on the antibody used. Methods to select conditions to permit binding is well within the ability of those skilled in the art. TF specific antibodies are commercially available, for example from Haematologic Technologies, Inc.

A "transient ischemic attack" (TIA, often colloquially referred to as "mini stroke") is caused by the temporary disturbance of blood supply to a restricted area of the brain, resulting in brief neurologic dysfunction that persists, by definition, for less than 24 hours; if symptoms persist then it is categorized as a stroke.

Ranges provided herein are understood to be shorthand for all of the values within the range. For example, a time of 1 to 50 seconds is understood to include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 seconds, and all fractional values between the numbers.

"Less than" or "up to" is understood as the range from zero up to and including the delimiter in the phrase. For example, "less than 5" includes 0, 1, 2, 3, 4, or 5, and all fractional values between 0 and 5.

"At least" or "or more" is understood as the lower delimiter and any value higher. For example, "more than 10" is understood as 10, 11, 12, . . . ∞, with the understanding that practical considerations can effectively limit the upper end of the range. For example, the upper limit of the range can be limited by the stability of the sample or reagents, the need for a physician to obtain results, the number of work hours in a day to run an experiment, the viability of a cell, or the time frame in which a change is expected to be observed. Such considerations are well understood by those of skill in the art.

Unless specifically stated or obvious from context, as used herein, the term "or" is understood to be inclusive.

Unless specifically stated or obvious from context, as used herein, the terms "a", "an", and "the" are understood to be singular or plural.

As used herein, "about" is understood to mean approximately or reasonably close to, and within the tolerances generally accepted in the specific experiment or result, for example within two standard deviations of the mean of a specific result. For example, about can be understood as a variation of 10% or less, 7% or less, 5% or less, 2% or less, or 1% or less.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any composition or method provided herein can be combined with any other composition or method provided herein.

Data are presented herein as mean±standard deviation, median (minimum-maximum), or percent as noted. Differences between continuous variable groups were examined using the Student t test (two-tailed). Logarithmic transformations were performed on data that were distributed non-normally. Odds ratios were constructed for categorical variables.

DETAILED DESCRIPTION

Figure 1A:
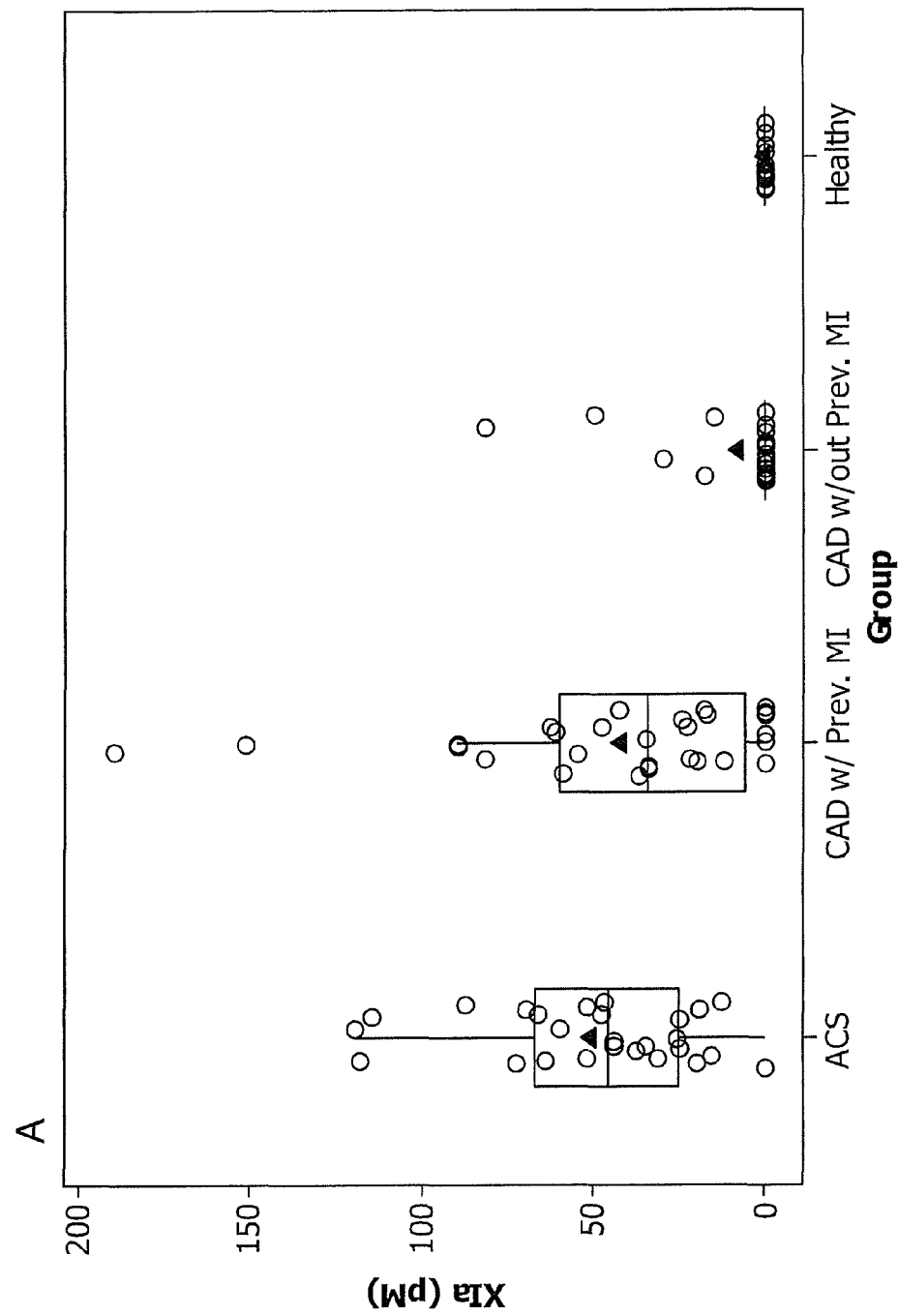
FIGS. 1A-1C are graphs showing FXIa (A), IL-6 (B), and TAT (C) concentrations in ACS, CAD-MI, and CAD-w/o MI patients, and healthy individuals. Boxes encompass the data between the first and third quartiles with an additional line denoting the median. The vertical line extends to the highest and lowest data point within the limit (1.5 times the interquartile range from the first and third quartile). The triangles represent the mean values.

The present invention provides methods for the diagnosis of cardiovascular disease, particularly heart failure, ACS and stroke, and stratification of subjects with stable CAD, or stroke (acute stroke vs. previous stroke; acute TIA vs. prior TIA) that feature methods of detecting FXIa and/or TF in a sample from the subject. The invention is based, at least in part, on the discovery that FXIa and TF activity can be detected in contact pathway-inhibited plasma from patients with a number of cardiovascular diseases including patients with stable CAD, ACS, heart failure, stroke, particularly acute stroke, and acute transient ischemic attack.

It has been established that inflammation and enhanced procoagulant activity are associated with the pathogenesis of atherosclerotic vascular disease. Assay specificity was based upon the prolongation of clotting time by the addition of inhibitory antibodies to FXIa and TF, respectively. Activity can also be detected by use of fluorogenic substrates of FXIa and TF activity. Correlations between FXIa and levels of both interleukin-6 and TAT (a thrombin generation marker) were established. The invention includes the discovery that levels of FXIa activity and TF activity can be used for stratification of subjects having or suspected of having CAD to determine the likelihood of progression to ACS. The assays for detecting the level of FXIa can also be used as a positive predictor of the occurrence of stroke, particularly acute stroke, as well as heart failure and acute transient ischemic attack, when combined with observation of other appropriate signs or symptoms of the particular disease or disorder.

The contributions of FXIa and TF activity in plasma of patients with coronary artery disease (CAD) were evaluated and compared. Citrate plasma was obtained prior to therapy from 53 patients with stable angina, 29 with a history of previous myocardial infarction (CAD-MI) and 30 with acute coronary syndrome (ACS), within 12 hours from pain onset. Four ACS patients treated with heparin were excluded. FXIa and TF activity were determined in clotting assays based upon the prolongation of clotting time by inhibitory monoclonal antibodies.

Twenty-five of 26 ACS patients (96%) and 22 of 29 CAD-MI patients (76%) had quantifiable FXIa ($50\pm33$ and $42\pm45$ µM, respectively). Ten of 26 (38%) ACS patients and only 3 of 53 (6%) stable CAD patients showed TF activity (<0.5 µM). No FXIa or TF activity was observed in age-matched healthy controls (n=12). For both CAD-MI and ACS patients, there were correlations (p<0.05) between FXIa and interleukin-6 ($R^2=0.59$ and 0.39, respectively) and between FXIa and TAT ($R^2=0.64$ and 0.63, respectively). These results demonstrated that the majority of ACS and CAD-MI patients have circulating FXIa levels that correlate with markers of coagulation and inflammation.

Citrate plasma from healthy individuals supplied with 0.1 mg/ml corn trypsin inhibitor (CTI) and 2 µM phosphatidylcholine phosphatidlyserine (PCPS) vesicles does not clot in 3000 upon the addition of 15 mM $CaCl_2$. When plasmas from CAD patients were tested with the same stimulus, most plasma samples had clotting times shorter than 3000 s and as short as 300 s. These plasmas thus had elevated procoagulant activity when compared with plasma from healthy individuals.

It is suggested that this coagulation activity could be related to TF-bearing microparticles potentially present in the patient plasma. However, while addition of an inhibitory monoclonal anti-TF antibody prolonged the clotting time of some of these plasmas, the majority of "active" relatively rapidly clotting plasmas were not affected by the addition of the anti-TF antibody. Moreover, even for those plasmas, which responded to the anti-TF antibody, the prolongation of the clotting time still did not extend to 3000 s.

This observation led to the conclusion that a TF-independent procoagulant activity was present in a significant fraction of CAD patients. Potential candidates for this activity were factors IXa, Xa, and XIa and thrombin. Further experiments, which employed the corresponding inhibitory monoclonal antibodies, showed that all CAD patient plasmas with elevated procoagulant activity responded to the addition of an inhibitory anti-FXI antibody leading to the prolongation of the clotting time to >3000 s for most of plasmas suggesting the presence of active FXIa in these samples.

The persistence of a serine protease in plasma, which contains an abundance of inhibitors for serine proteases, is an unusual observation and raises the question of whether FXIa can survive in that environment. Experiments were conducted to test the stability of FXIa in citrate plasma. Plasma from healthy donors to which exogenous FXIa was added showed that 80 to 90% of FXIa survives in citrate plasma over the time required for plasma preparation from blood (30-40 min). Additionally, the de novo formation of FXIa activity was not observed in citrate plasma either in the presence or absence of contact pathway inhibition at room temperature over a period of 75 minutes. These data indicate that the FXIa observed in plasma from ACS and stable CAD patients reflects the in vivo levels of this enzyme and is not an artifact of plasma preparation.

Our data indicated that there are significant differences in the frequencies at which FXIa and TF are found in the plasma of stable CAD patients, those with ACS, and healthy individuals. While no detectable FXIa or TF activity is observed in plasma from healthy volunteers, the vast majority of ACS patients display FXIa and a significant fraction display TF activity in plasma. A further stratification of stable CAD patients indicates that the majority of those with the history of previous MI have circulating FXIa, whereas only 21% of stable CAD patients without previous MI display FXIa activity. These data strongly suggest that FXIa levels can be used to predict which patients will progress to ACS.

The most surprising observation was that an active serine protease, FXIa, was present in the plasma of CAD patients, i.e. an environment containing high concentrations of irreversible inhibitors for serine proteases. (Colman R W, et al., editors. *Hemostasis and thrombosis basic principles and clinical practice*. Lippincott Williams & Wilkins, 2006: 3-16.) In vitro, FXIa can be generated from its precursor FXI either by thrombin (Gailani D and Broze G J, Jr. *Science* 1991; 253(5022):909-912) or by FXIIa in conjunction with prekallikrein and high molecular weight kininogen, the initiating enzymatic complex of the contact pathway. (Ratnoff O D, and Coply J E. *J Clin Invest* 1955; 34:602-6 13) While bleeding pathology does not seem to be associated with deficiency states of the contact pathway proteins, it has been suggested that FXII deficiency is a risk factor for thrombosis and ACS. (Halbmayer W M, et al., *Wien Med Wochenschr* 1993; 143(2):43-50; Goodnough L T, et al., *Medicine* (Baltimore) 1983; 62(4):248-255) Recent studies using transgenic FXII and FXI-deficient mice suggest that FXII plays a central role in pathologic thrombus formation, and that FXI activation by the contact pathway is a part of this process. (Renne T, et al. *J Exp Med* 2005; 202(2):271-281; Kleinschnitz C, et al., *Journal of Experimental Medicine* 2006; 203(3):513-518) Studies reported by several groups attempting to establish correlations between FXIIa and coronary risk have led to contradictory results. Cooper and coworkers suggested that FXIIa is associated with increased coronary risk but found that low levels of FXIIa are not protective.[26] A study published by Lowe et al. concluded that FXIIa is not associated with coronary risk.[27] Similarly, it has been reported that ACS is not associated with contact pathway activation (Alfieri P, et al., *Thromb Res* 2005; 1 15(1-2):65-72) and that the markers of contact pathway activation, including FXIIa, are not increased in ACS patients with elevated FXI activation.

The correlation between FXIa and IL-6 in our study indicates that CAD patients with circulating FXIa have an increased TF expression on blood and vascular cells. (Steffel J, et al., *Circulation* 2006; 113(5):722-73 1; Grignani G, and Maiolo A. *Haematologica* 2000; 85(9):967-972) Additionally, the correlation between FXIa and TAT levels suggest a connection between thrombin generation and FXI activation. A possible explanation for FXIa activity in CAD patients is that with elevation of inflammatory cytokines, TF expression and, as a consequence, thrombin generation is enhanced, causing enhanced activation of FXI. A possible influence of the contact pathway cannot be eliminated.

The lack of correlation between FXIa and TF activity is, most likely, related to the properties and in vivo location of TF. It is well established that TF is a membrane protein and may be expressed/exposed on the surface of endothelial cells and circulating blood cells, primarily monocytes, upon cytokine stimulation. Soluble TF, which lacks the ability to bind to cell or artificial membranes, has little (if any) activity in blood coagulation processes[30;31] (Morrissey J H, et al; *Blood* 1993; 81(3):734-744; Butenas S, et al., *Blood* 104[1 1], 39a. 2004. (Abstract)) It has been suggested by several groups of investigators that limited TF activity in plasma is associated with TF located on microparticles, and that microparticles bearing TF circulate in vivo, primarily in blood of patients with inflammation[32-34] (del Conde I, et al., *Blood* 2005; 106(5):1604-161 1; Osterud B and Bjorklid E. *Semin Thromb Hemost* 2006; 32(1):11-23; Simak J, and Gelderman M P. *Transfus Med Rev* 2006; 20(1): 1-26.) Under conditions of a routine plasma preparation, microparticles are not removed with blood cells, remain in plasma preparations and, as a consequence, transfer TF activity from blood to plasma. However, experimental evidence is lacking, which suggests a correlation between TF concentration and activity in plasma and those in vivo.

A study by Minnema et al. reported that only a small fraction of patients with acute MI and unstable angina pectoris contained detectable amounts of a FXI activation marker (FXIa-C1 inhibitor complex). The discrepancy between the results of that study and the present observations is related to the technical approaches used to measure FXIa in plasma. The presently claimed assay measures the FXIa activity, whereas Minnema and coworkers quantitated the FXIa-C1 inhibitor complex. C1 inhibitor is one of several serine protease inhibitors that form covalent complexes with FXIa. Although Wuillemin et al. suggest that C1 inhibitor is the most efficient in vivo inhibitor of FXIa (*Thromb Haemost* 1996; 76(4):549-555) others report that only 8% of FXIa is present in complex with C1 inhibitor. Thus, the FXIa-C1 inhibitor complex lacks sensitivity and reports only a fraction of FXIa present in plasma.

A comparison of FXIa concentrations in ACS patients of the study with the levels of the FXIa-C1 inhibitor complex reported for similar patients suggests that the majority of FXIa formed circulates in vivo as a free enzyme or in reversible complex(es) with reversible inhibitor(s). Without wishing to be bound by theory, this conclusion is also supported by data reported herein, which indicate that FXIa disappearance from plasma is a relatively slow process.

Results reported herein indicate that the detection of FXIa assay can be used for stratification of subjects to predict an elevated thrombotic risk in apparently stable CAD patients. In comparison with conventional clinical laboratory tests, the present FXIa assay is rapid, relatively simple and has the potential to be incorporated as a point-of-care assay or rapid, in-house laboratory test for the stratification of CAD patients. Results can be used to determine or monitor the need of a subject for anticoagulant therapy. If desired, detection of FXIa activity can be used in combination with an assay that detects TF activity.

Upon demonstrating an elevation of FXIa in CAD and CAD-MI, further studies were performed to determine if elevated levels of FXIa and TF could be found in subjects having other cardiovascular diseases (see Table 3). Two hundred eleven of 470 stroke patients (45%) were found to have elevated levels of FXIa, with elevated levels of FXIa being maintained for an extended period (i.e., over three months). An increase in the level of FXIa was found in 73% (106 of 145) of subjects suffering from acute stroke, whereas only 35% (57 of 165) of those that had previously suffered a stroke more than 3 months prior to obtaining the sample had elevated levels of serum FXIa. Similarly, subjects with acute TIA showed increased levels of FXIa more consistently than those that suffered from TIA more than three months prior to obtaining the sample (49%, 39 of 79 vs. 11%, 9 of 79). As noted above, no FXIa was detected in pooled normal samples. An increase in TF was also observed in some subjects, but not as consistently as the increase in FXIa. Therefore, a detection of an increase in TF in conjunction with an increase in FXIa can be supporting evidence of a stroke or TIA, but the absence of an increase in TF is not necessarily meaningful in the diagnosis of the conditions.

Subjects suffering from heart failure were found to have an increase in FXIa and TF with about the same frequency. Twenty of 53 (38%) and 22 of 53 (42%) of patients suffering from heart failure were found to have increased levels of TF and FXIa respectively. Therefore, an increase in either protein, can assist in the confirmation of a diagnosis of heart failure. Similarly aortic stenosis increased the level of FXIa or TF in about the same number of patients, 26% (14 of 53) and 23% (12/53), but not in most patients.

Cardiac surgery, specifically CABG, was found to increase TF in 20% of subjects (25 of 122) and FXIa in 40% of subjects (49 of 122).

These data demonstrate that the release of FXIa or TF can occur as a result of cardiovascular stress or disease from any of a number of sources. Although not always present in all subjects after cardiac stress, it is not present in normal subjects not suffering from cardiovascular disease. Moreover, the level of FXIa is present more frequently at the time of an acute event, ACS, acute stroke, and MI. This makes the presence of FXIa a strong indicator of an acute event. Also useful is the persistence of FXIa and TF after an event. For example, MI, especially in diabetic subjects can go undetected. Similarly, heart failure can persist for a long time before overt symptoms are present. Therefore, detection of an elevated level of FXIa or TF could be a useful initial screening method to detect patients who should undergo further screening for cardiovascular conditions or diseases. Moreover, it is noted that in subjects who had an increased (i.e., detectable) level of TF also had a detectable level of FXIa. Therefore, the detection of both FXIa and TF in a sample from a subject can be useful as a diagnostic for cardiovascular disease. FXIa and TF need not be present in quantifiable amounts to be useful as diagnostic markers.

The methods described herein for determining the presence of FXIa or TF activity in a sample can be modified for high throughput analysis of samples for routine screening. Modifications of the method below to accommodate specific reagents, reaction volumes, coagulation monitoring devices, and other variables well known to those skilled in the art is within the scope of the instant invention.

The methods provided herein provide reproducible methods for the detection and quantitation of FXIa and TF in a patient sample, preferably in a serum sample. The methods herein provide a constant of variation between replicate samples of less than 15%, less than 12%, less than 10%, less than 8%.

The methods provided herein can be used for monitoring a subject for persistence of FXIa and/or TF in the blood. Cardiovascular disease frequently results in multiple acute events in a subject. The initial acute event can elevate the level of FXIa and/or TF in the blood. It would be expected that over time a decrease, or at least no increase, in FXIa or TF would be observed in a subject in the absence of acute events (e.g., MI, stroke, TIA). As such event can go unnoticed by the subject, especially if they are minor, e.g., a TIA during sleep, an increase in the level of FXIa or TF could be indicative of a subsequent acute event.

In a preferred embodiment, a blood sample is drawn from a subject into a tube containing sodium citrate to inhibit coagulation. The plasma is separated from the red cells, for example, by centrifugation. The sample can be tested that same day or frozen for later analysis. At least a portion of the sample is treated with an inhibitor of the contact coagulation pathway that does not inhibit FXIa activity, to prevent clotting through contact pathways. In a preferred embodiment, the treated sample is then portioned into test and control samples (or two sets of duplicate or triplicate samples). The first sample is treated with an FXIa specific antibody under conditions to permit binding of the antibody to FXIa and incubated at 37° C. to allow binding of antibody to the FXIa, at least about 30 seconds, at least about 1 minute, at least about 2 minutes, at least about 5 minutes, preferably less than 1 hour, 2 hours, 4 hours, 6 hours, or overnight. It is understood that the binding time and conditions may vary with the specific antibody used. Such parameters can be readily modified by those of skill in the art.

After antibody incubation of the test sample, both the test and control sample are contacted with $Ca^{++}$, preferably in the form of $CaCl_2$. After a brief incubation, about 30 seconds to 10 minutes, preferably about 30 seconds to 5 minutes, more preferably about 1 minute, a phospholipid surface, preferably phospholipid vesicles prepared from purified phospholipids having at least some acidic head groups (e.g., PS), is added to both test and control samples to promote coagulation. Clotting time is monitored, preferably for at least about 2000 seconds, 2500 seconds, 3000 seconds, or longer; or until coagulation has taken place in both the test and control samples. Clotting is monitored in the device by determining an increase in the viscosity of the clotted plasma sample.

In lieu of treating a portion of the citrate-contact pathway inhibitor treated sample with an FXIa antibody, a citrate-contact pathway inhibitor treated sample from a subject can be tested for clotting time against a standard control containing a known quantity of FXIa. The standard control would preferably be pooled citrate-contact pathway inhibitor treated plasma from healthy donors. Recombinantly expressed or purified FXIa can be added back to the healthy donor pooled plasma at known quantities prior to the performance of the clotting assay. Such a control sample can be used in addition to the antibody treated and non-antibody treated samples from a subject as set forth above.

An assay for TF activity is performed essentially by the same method as the FXIa assay except that a TF specific antibody is used rather than a FXIa specific antibody. Briefly, blood sample is drawn from a subject into a tube containing sodium citrate to inhibit coagulation. The plasma is separated from the red cells, for example, by centrifugation. The sample can be tested that same day or frozen for later analysis. At least a portion of the sample is treated with an inhibitor of the contact coagulation pathway that does not inhibit TF activity, to prevent clotting through contact pathways. In a preferred embodiment, the treated sample is then portioned into test and control samples (or two sets of duplicate or triplicate samples). The first sample is treated with an TF specific antibody under conditions to permit binding of the antibody to TF and incubated at 37° C. to allow binding of antibody to the TF, at least about 30 seconds, at least about 1 minute, at least about 2 minutes, at least about 5 minutes, preferably less than 1 hour, 2 hours, 4 hours, 6 hours, or overnight. It is understood that the binding time and conditions may vary with the specific antibody used. Such parameters can be readily modified by those of skill in the art.

After antibody incubation of the test sample, both the test and control sample are contacted with $Ca^{++}$, preferably in the form of $CaCl_2$. After a brief incubation, about 30 seconds to 10 minutes, preferably about 30 seconds to 5 minutes, more preferably about 1 minute, a phospholipid surface, preferably phospholipid vesicles prepared from purified phospholipids having at least some acidic head groups (e.g., PS), is added to both test and control samples to promote coagulation. Clotting time is monitored, preferably for at least 2000, 2500, 3000 seconds or more, or until coagulation has taken place in both the test and control samples. Clotting is monitored in the device by determining an increase in the viscosity of the clotted plasma sample.

In lieu of treating a portion of the citrate-contact pathway inhibitor treated sample with an TF antibody, a citrate-contact pathway inhibitor treated sample from a subject can be tested for clotting time against a standard control containing a known quantity of TF. The standard control would preferably be pooled citrate-contact pathway inhibitor treated plasma from healthy donors. Recombinantly expressed or purified TF incorporated into vesicles can be added back to the healthy donor pooled plasma at known quantities prior to the performance of the clotting assay. Such a control sample can be used in addition to the antibody treated and non-antibody treated samples from a subject as set forth above.

Example 1

Selection of Subjects

ACS

We studied 30 patients with ACS were admitted to the Department of Hemodynamics of the Jagiellonian University and 53 patients with angiographically confirmed stable CAD (>50% stenosis in at least one major coronary artery) recruited from an outpatient clinic. Twenty-nine of the stable CAD patients (55%) had a history of previous myocardial infarction (MI) 0.5-3 years before enrollment. ACS patients had experienced chest pain for up to 12 hours prior to seeking treatment.

Upon arrival at the hospital, patients were enrolled and blood was taken before treatment was initiated. All patients took 300 mg aspirin before the study. None of the subjects received thienopyridines or other anticoagulants prior to blood collection. Four ACS patients received 5000 U of unfractionated heparin prior to the blood draw and were excluded.

Inclusion criteria for ACS patients were typical chest pain and either ST-segment elevation ~0.1 mV or ST-segment depression ~0.1 mV in at least two contiguous leads, and elevated cardiac troponin levels. ST-segment elevated myocardial infarction (STEMI) was diagnosed in 14 patients and the remainder were considered non-STEMI (NSTEMI). Exclusion criteria for all individuals were as follows: cardiogenic shock or heart failure (NYHA III/IV), any acute illness, cancer, hepatic or renal dysfunction, history of venous thromboembolism or stroke, oral anticoagulant administration, previous coronary artery bypass surgery. Stable angina patients (Canadian Cardiovascular Society classes II or III) were matched to the ACS patients for age and sex. None of these patients developed ACS or underwent angioplasty within the 6 months prior to the study. Twelve healthy controls were matched to the CAD patients for age and sex. The characteristics of both patient groups and those of healthy controls are shown in Table 1.

CAD

Seventy-nine CAD patients were divided into three groups, i.e. those with ACS (n=26), stable CAD patients with a history of previous MI (n=29; CAD-MI) and stable CAD patients without previous MI (n=24; CAD-w/oMI). A group of healthy individuals (n=12) was also analyzed (Tables 1 and 2). Individuals in all four groups were balanced in terms of age and body mass index (BMI). The percentage of current smokers was lower (21%) in CAD-without MI group than in other three groups (33-38%). No hypertension, diabetes or previous MI was diagnosed in healthy individuals. They also had the lowest concentration of fibrinogen (2.8 g/L). The ACS group had the highest frequency (73%) of hypertension among all three patient groups. The ACS group also had the highest total cholesterol (6.2 mM), LDL (3.9 mmol/L), triglyceride (2.2 mM), glucose (6.65 mmol/L) and C reactive protein (CRP) (3.0 mg/L) concentration and detectable troponin T amounts (4.5 mg/L). There were no significant differences in clinical parameters between the CAD-MI and the CAD w/o MI groups with exception in number of patients with previous revascularization (69% and 38%, respectively). The Activated Partial Thromboplastin Time (APTT) and platelet count were similar for all four groups.

Stroke

We included white adult patients with acute ischemic stroke. Exclusion criteria were as follows: acute illness, cancer, renal dysfunction (>177 umol/L, or 2 mg/dl) anticoagulant therapy, acute coronary syndrome within the preceding 6 months, treatment with oral anticoagulants, heparins or clopidogrel, history of hemorrhagic diathesis or documented thromboembolism. Aspirin was allowed.

Ischemic stroke was diagnosed according to WHO criteria. Stroke etiology was diagnosed according to the TOAST criteria as large vessel disease (LVD) stroke, small vessel disease (SVD) stroke, cardioembolic (CE) stroke and stroke of unknown or rare etiology (i.e. dissection). All patients underwent computed tomography (CT) of the head on admission to exclude other causes of sudden focal neurological deficit. The diagnostic work-up included ultrasound examination of the carotid and vertebral arteries, electrocardiography and transthoracic echocardiography. In patients <50 years, transesophageal echocardiography, as well as the laboratory thrombophilia screening and evaluation to exclude systemic vasculitides were performed. Only patients with acute stroke who were drawn for laboratory investigations within 72 hours after stroke onset were included in the analysis.

We enrolled patients with documented (CT/NMR) history of ischemic stroke that occurred not earlier than 3 months before the blood collection. The exclusion criteria the same as in the acute stroke patients.

CABG

We enrolled patients undergoing elective primary CABG with or without the use of cardiopulmonary bypass. Inclusion criteria were: age >18 years, stable angina pectoris and need for elective primary myocardial revascularization for coronary artery disease. Patients were randomly recruited from consecutive elective cases. Inclusion criteria for stable angina were exercise-induced chest pain with >1 mm ST-segment depression in at least two contiguous standard leads or >2 mm ST-segment depression in at least two contiguous precordial leads in combination with symptoms according the Canadian Cardiovascular Society classification.

Exclusion criteria are the same as presented for the acute stroke project. Additionally, patients requiring valve implantation or other simultaneous surgical procedure were also ineligible. Aspirin was withdrawn in all patients 7-10 days before operation.

Congestive Heart Failure

Patients were eligible if they had a history of signs and symptoms of CHF, left ventricular ejection fraction <40%, were hemodynamically stable within 3 months preceding the study. Exclusion criteria were anticoagulant therapy, atrial fibrillation, cancer, acute coronary syndromes within the last 3 months, autoimmune disorders or infections (CRP>10 mg/L).

Example 2

Sample Collection and Characterization

Blood was drawn from an antecubital vein with minimal stasis within 15 minutes upon admission in the case of ACS patients, and as soon as reasonably possible for all other acute event subjects, preferably within 15 minutes of admission, and after an overnight fast between 7 to 9 a.m. in the case of stable CAD patients and healthy volunteers. Serum and citrate plasma samples (9:1 of 3.2% sodium citrate a calcium chelator that inhibits coagulation) were centrifuged at 2540 g for 15 minutes at 24° C. within 20 minutes of collection, immediately frozen, and stored in aliquots at −80° C. until further use. Lipid profiles, blood morphology, glucose, creatinine, albumin, aminotransferases, and creatine kinase were assayed by routine laboratory techniques. Fibrinogen was determined using the Clauss method. High-sensitivity CRP was measured by latex nephelometry (Dade Behring, Marburg, Germany). Commercially available immunoenzymatic assays were used to determine plasma interleukin-6 (IL-6; R & D Systems, Abingdon, UK), F1.2 and TAT (Dade Behring) by investigators blind to all subject data. All the intra-assay and inter-assay coefficients of variation were below 7%.

Example 3

Factor XIa Plasma Clotting Assay

Citrate plasma (200 ul) was thawed at 37° C. in the presence of 4 ul corn trypsin inhibitor (5 mg/ml) (CTI; prevents contact pathway initiation of coagulation; prepared as previously described in Cawthern et al. (*Blood* 1998; 91:4581-4592, incorporated herein by reference). Plasma was divided into 2-100 ul aliquots, one test and one control.

An aliquot of the CTI-containing plasma was placed in a cuvette in an ST8 instrument (Diagnostica Stago, Parsippany, N.J.) and maintained at 37° C. CaCl$_2$ was added to a final concentration of 15 mM (1.5 ul of 1M stock) and the plasma incubated for 1 min; clotting was initiated by the addition of 2 µM phospholipid vesicles (PCPS) (4 ul of 5 uM stock) composed of 25% dioleoyl-sn-glycero-3-phospho-L-serine and 75% of 1,2-dioleoyl-sn-glycero-3-phosphocholine (both from Avanti Polar Lipids, Inc; Alabaster, Ala.) and prepared as described in Higgins and Mann (*J Biol Chem* 1983; 258 (10):6503-6508, incorporated herein by reference).

In parallel, inhibitory monoclonal anti-FXI (aFXI-2) antibody was added to a final concentration of 0.1 mg/ml (1 ul of 10 mg/ml stock) to the other CTI-containing citrate plasma aliquot in a cuvette. Sample was incubated for 1 minute to allow the antibody to bind the FXIa. CaCl$_2$ was added to a final concentration of 15 mM and the plasma was incubated for 1 minute; clotting was initiated by the addition of 2 µM phospholipid vesicles (PCPS) as above.

In both samples, clotting times were determined using the ST8 instrument in accordance with the manufacturer's instructions. FXIa activity in plasma was calculated from calibration curves developed with human FXIa (a gift from Dr. R. Jenny from Haematologic Technologies, Inc., Essex Junction, Vt.) or relipidated TF. Similar experiments were performed using anti-TF antibody and TF activity was calculated from the calibration curve using recombinant TF$_{1-242}$ (a gift from Dr. R. Lundblad from Baxter Healthcare Corp., Duarte, Calif.) in pooled 10-donor normal plasma (see, e.g., U.S. Pat. No. 7,235,377, incorporated herein by reference).

If in the control sample plasma clotted prior to 2000 s after the initiation, and the clotting time of the test sample was extended beyond 3000 s (the time-limit of the assay) by the addition of the anti-FXIa antibody, the clotting activity observed in the control experiment was assigned to factor XIa. To quantitate FXIa concentration in CAD patient plasmas, a calibration curve was constructed by the addition of varying concentrations of purified plasma FXIa to 10-donor plasma from healthy individuals (FXI present at 94% of mean physiologic concentration). The addition of 10 µM FXIa to this plasma lead to a clotting time of 2200 s. With increasing FXIa concentration, the clotting time steadily decreased to 260 s at 500 µM FXIa. When 0.1 mg/ml ctFXI-2 (a FXIa specific antibody) was added to plasma treated with 500 µM FXIa, no clot was observed over 3000 s.

The analysis of FXIa in patient and healthy volunteer plasma showed that 25 of 26 (96%) patients with ACS contained quantifiable amounts (>10 µM) of FXIa (FIG. 1A; Table 3). The concentration of FXIa varied from 16 to 120 pM with an average value of 50±33 µM (mean±SD). Analyses of plasma from 29 CAD-MI patients showed that 22 (76%) contained quantifiable amounts of FXIa at concentrations ranging from 15 to 190 µM with a mean average value of 42±45 µM. In contrast, only 5 of 24 CAD-w/oMI patients (21%) contained detectable amounts of FXIa. The odds ratio of detecting plasma FXIa in stable survivors of MI was 11.9 (95% confidence interval, 3.2-43.9). No FXIa activity was detected in plasma from 12 healthy volunteers.

Example 4

Fluorogenic Assay for Amidolytic Activity for the detection of FXIa

To test the conclusion that the clotting activity observed in the plasmas of CAD patients and its response to the anti-FXI antibody was related to the presence of an active enzyme, 10-donor normal (i.e., control) and a CAD patient plasma were tested for the amidolytic activity in a fluorogenic assay. 40 µl of citrate plasma (10-donor normal or CAD patient) was added to 1940 µl of HBS/CaCl$_2$ buffer (20 mM HEPES, 150 mM NaCl, 2 mM CaCl$_2$ and 0.1% PEG 6000; all reagents purchased from Sigma) and placed into a cuvette. When desired, purified human FXIa was added to plasma. 20 µl of a fluorogenic substrate (6,1-D-LPR-propylaminonaphthalene-sulfonamide; synthesized in house, see, U.S. Pat. Nos. 5,399,487 and 6,566,493, both herein incorporated by reference) was added at a final 100 µM concentration and the rate of substrate hydrolysis was evaluated in a spectrofluorometer FluoroMax-2 (Jobin Yvon-Spex Instruments S.A., Inc., Edison, N.J.) at $\lambda_{ex}$ 350 nm and $\lambda_{em}$ 470 nm with a 450 nm cut-off filter in the emission light beam. FXIa concentration was determined from a calibration curve built by sequential dilutions of purified human FXIa in 10-donor normal plasma.

No substrate hydrolysis was observed when 10-donor normal plasma was mixed with the substrate solution. An addition of 50 pM purified FXIa to this plasma lead to substrate hydrolysis at a rate of 79 pM/s. When CAD patient plasma was tested in this assay, the rate of substrate hydrolysis observed was 150 pM/s, suggesting that the concentration of active FXIa in this plasma was 95 pM. Clotting assay of this plasma indicated that FXIa concentration is 140 pM. An incubation of this CAD patient plasma for 30 min at 25° lead to a decrease in FXIa concentration by 10% (to 85 pM). These data are in an agreement with the clotting experiment results both suggesting that in citrate plasma FXIa activity is only minimally compromised during the time required for plasma preparation (~30 min).

Example 5

Tissue Factor Plasma Clotting Assay

The reliable quantitation limit of our TF activity assay based upon the titration of relipidatal TF1-242 (Tissue Factor amino acids 1-242) into CTI-inhibited 10-donor citrate plasma is 0.4 pM. At this TF concentration, plasma clots in 1420 seconds. The addition of 4 pM TF to 10-donor plasma decreases the clotting time to 215 seconds. In the presence of 0.1 mg/ml aTF-5 (a TF specific antibody), no clot is observed in 3000 s when 4 pM TF is added.

Plasma from 10 of 26 ACS patients (38%) displayed detectable TF activity (Table 2). However, only 4 had TF activity at quantifiable concentrations; ranging from 0.5 to 0.9 pM. The concentrations of TF in the remaining samples were below 0.4 pM (the reliable quantitation limit). For CAD-MI patients, 2 of 29 (6.9%) and for CAD-w/oMI patients one of 24 (4.2%) displayed TF activity below 0.4 pM. All three of these plasmas contained FXIa in the range from 48 to 82 pM. No TF activity was observed in the plasma from healthy individuals.

Example 6

Fluorogenic Assay for Amidolytic Activity for the detection of TF

Tissue Factor is known to enhance FVIIa activity. Cleavage of by a fluorogenic substrate such as SN-17a (HTI catalog) (D-FPR-ANSNC$_6$H$_{11}$ and SN-17c (D-FPR-ANSNC$_4$H$_9$) (see also, e.g., U.S. Pat. No. 5,399,487, incorporated herein by reference) by FVIIa can be used to detect the presence of TF in a sample. Alternatively, commercially available kits such as the Atichrome® TF assay (Product No. 864) from American Diagnostica can be used to detect the presence of TF activity in a sample using manufacturer's instructions.

Detection of TF using a fluorogenic substrate can be performed as follows. 10-donor normal and a CAD patient plasma is tested for the amidolytic activity in a fluorogenic assay and compared to a test sample containing or suspected of containing TF activity. 40 µl of citrate plasma (10-donor normal or CAD patient) is added to 1940 µl of HBS/CaCl$_2$ buffer (20 mM HEPES, 150 mM NaCl, 2 mM CaCl$_2$ and 0.1% PEG 6000) and placed into a cuvette. When desired, purified human TF is added to plasma. 20 µl of a fluorogenic substrate is added at a final 100 µM concentration and the rate of substrate hydrolysis was evaluated in a spectrofluorometer FluoroMax-2 (Jobin Yvon-Spex Instruments S.A., Inc., Edison, N.J.) at $\lambda_{ex}$ 350 nm and $\lambda_{em}$ 470 nm with a 450 nm cut-off filter in the emission light beam. TF concentration is determined from a calibration curve built by sequential dilutions of purified human TF in 10-donor normal plasma.

Substrate hydrolysis is indicative of the presence of TF activity in the sample.

Example 7

Markers of Inflammation and Coagulation and Their Correlation with FXIa

Figure 1B:
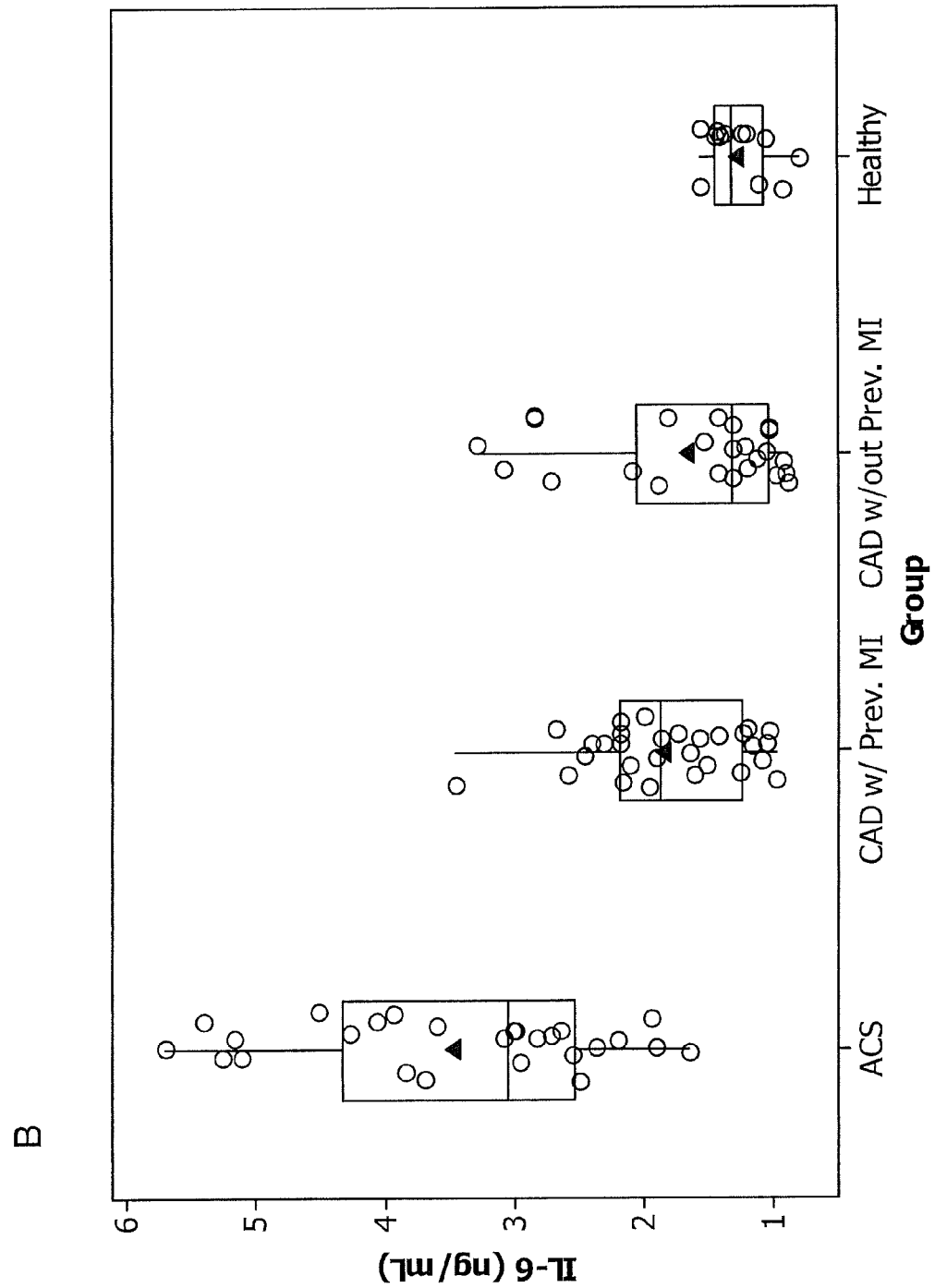
Figure 2A:
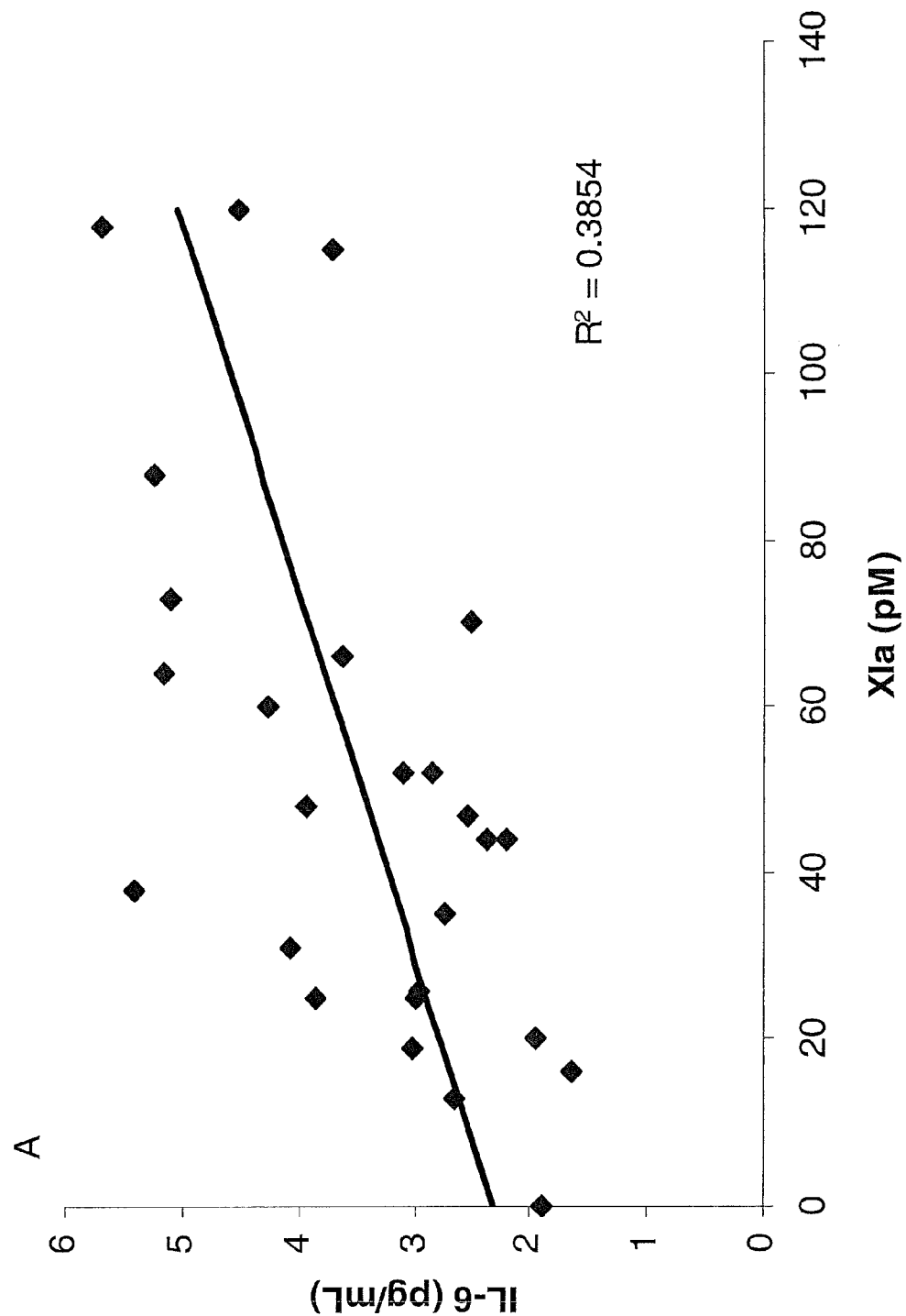
FIGS. 2A-2D are graphs showing a correlation between FXIa and IL-6 (A and B) and between FXIa and TAT (C and D) in ACS (A and C) and CAD-MI (B and D) patients.
Figure 2B:
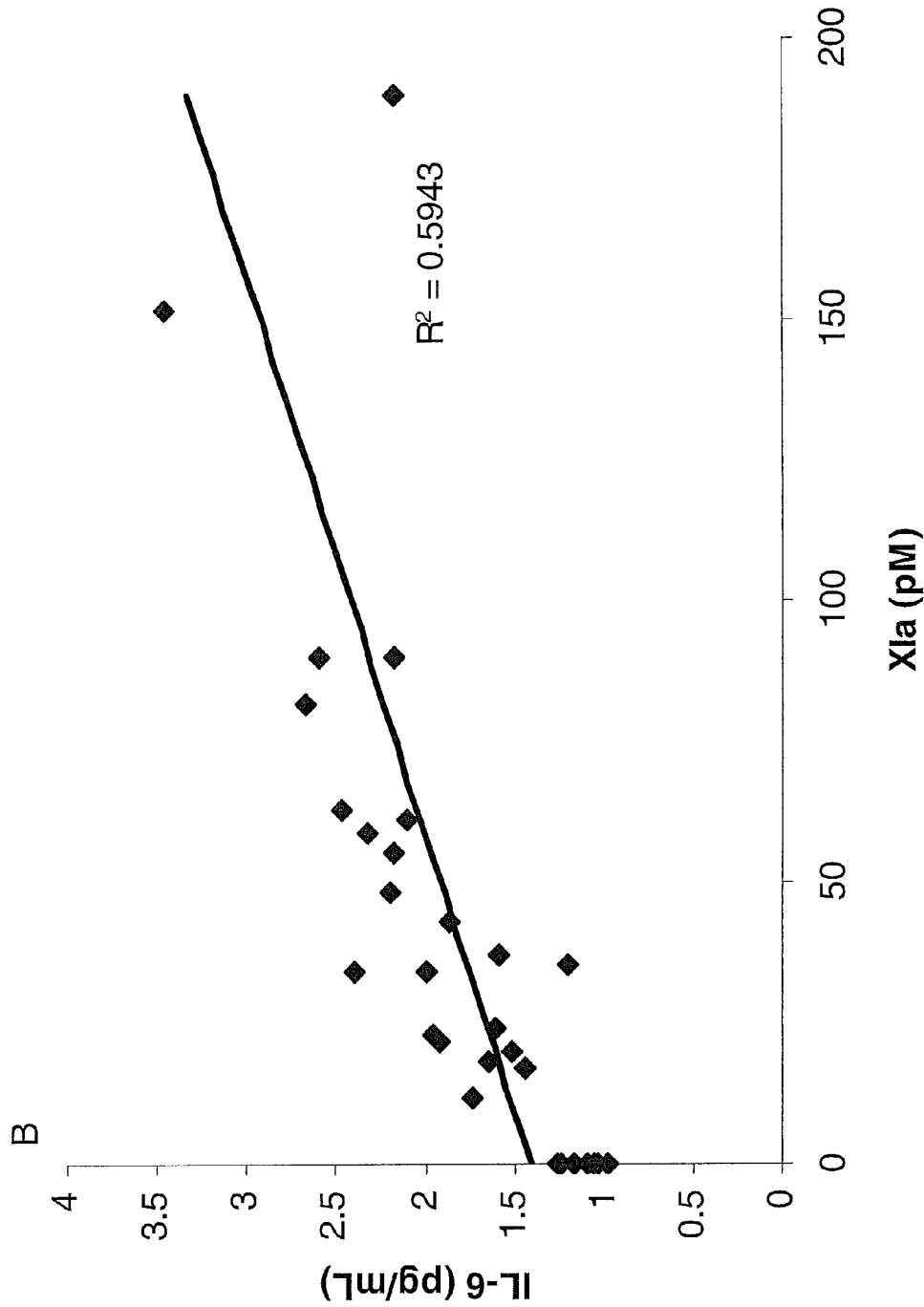

The concentration of IL-6 in plasma from patients with ACS (3.46±1.19 pg/ml) was significantly higher (p<0.001) than any other group (FIG. 1B and Table 2). The IL-6 concentrations in CAD-MI and CAD-w/oMI groups were similar (1.83 and 1.64 pg/ml, respectively). The lowest IL-6 levels were observed in plasma from healthy individuals (1.25±0.25 pg/ml). There was a positive correlation (p<0.05) between the FXIa and IL-6 concentrations in both groups of patients, ACS ($R^2$=0.39; FIG. 2A) and CAD-MI ($R^2$=0.59; FIG. 2B).

Figure 1C:
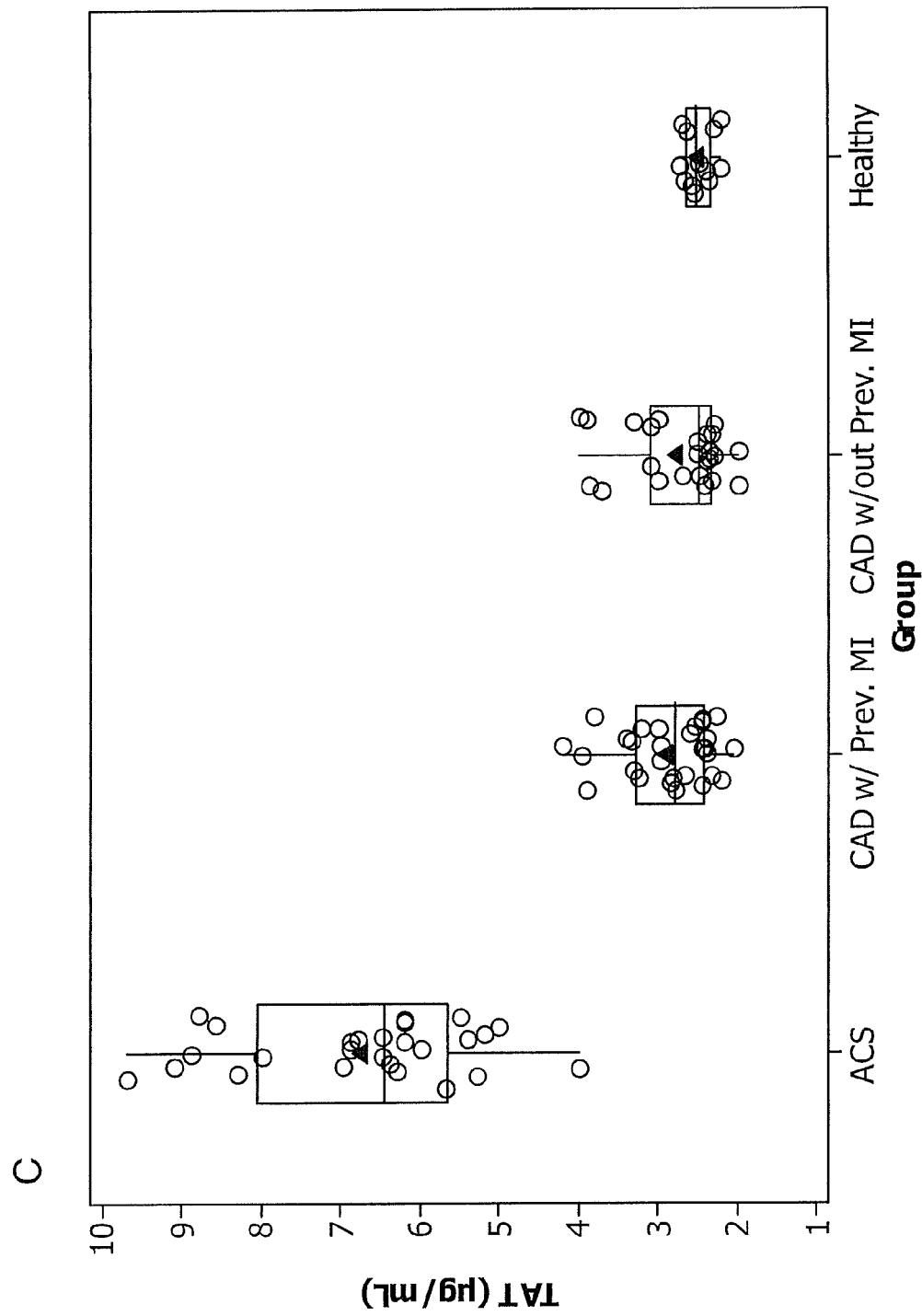
Figure 2C:
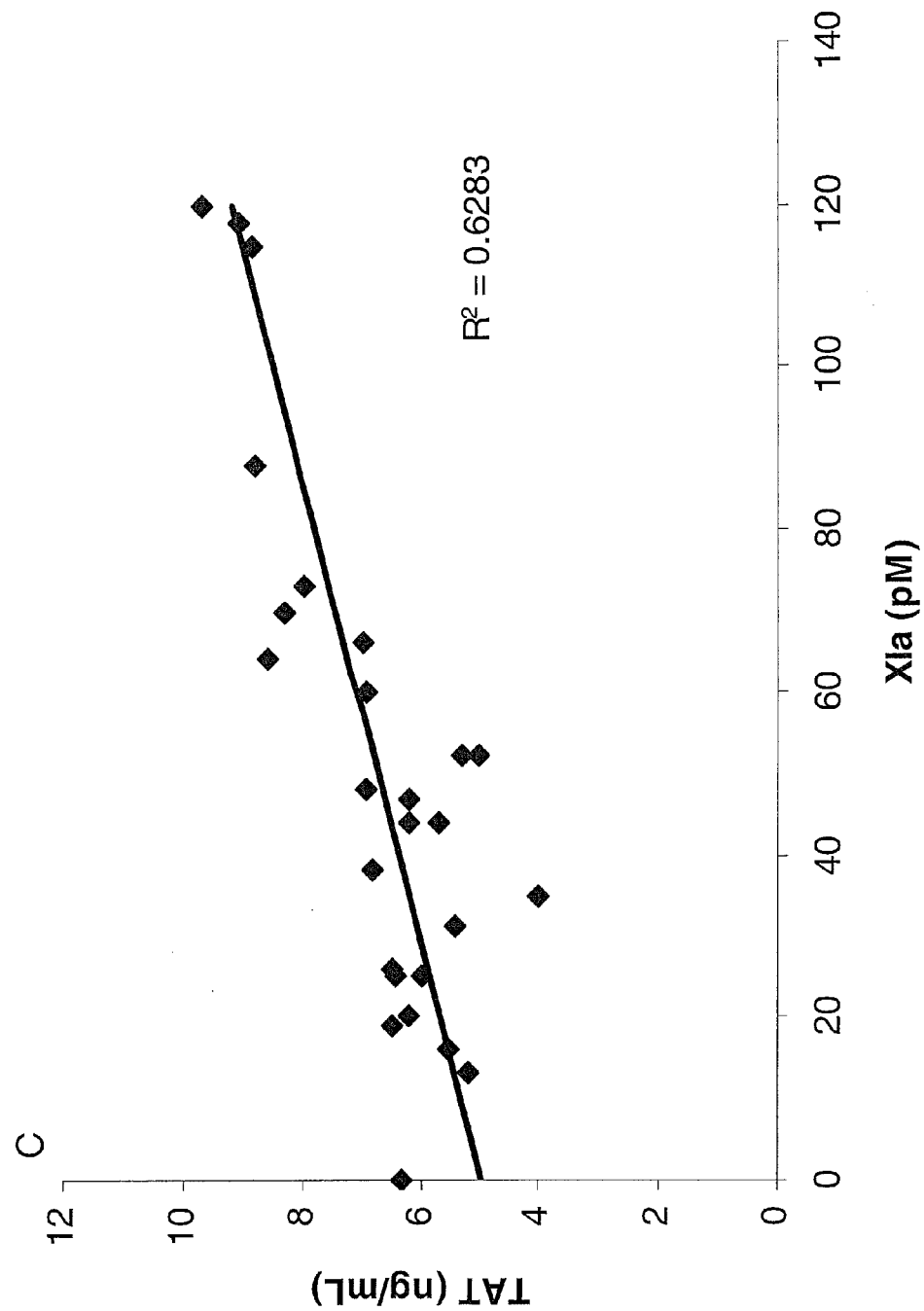
Figure 2D:
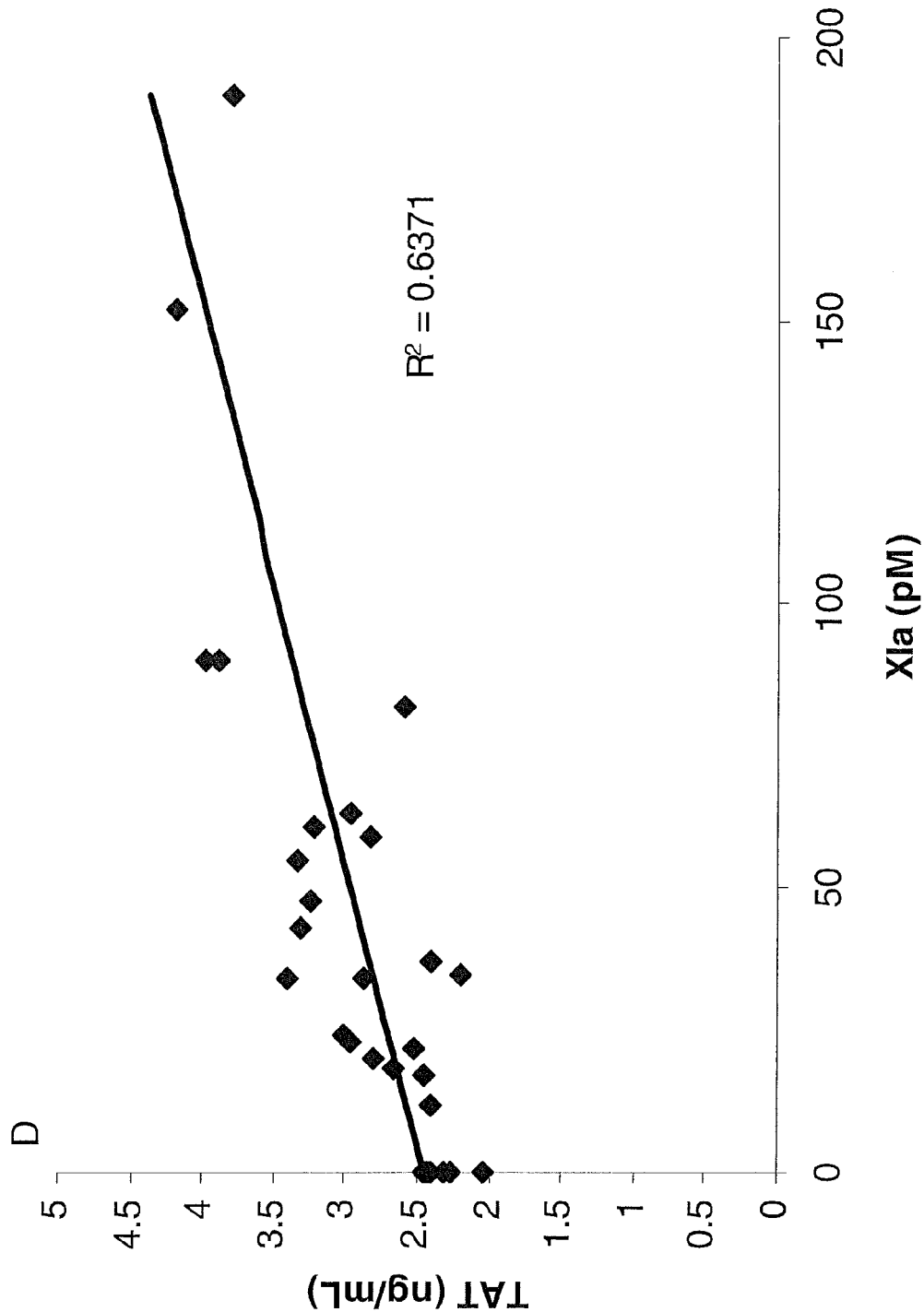

Similar to IL-6, the concentration of TAT (6.7±1.4 ng/ml) in the ACS group was significantly higher (p<0.001) than in any other group (FIG. 1C). There was no significant difference between the TAT concentration in stable CAD patients and healthy volunteers (2.8 and 2.5 ng/ml, respectively). The correlation coefficient $R^2$ between FXIa and TAT (p<0.05) was 0.63 for the ACS group (FIG. 2C) and 0.64 for the CAD-MI group (FIG. 2D). The pattern of the F1.2 concentration (prothrombin fragment 1.2) in the analyzed groups was similar to that of TAT, i.e. its concentration in the ACS group was significantly higher (p<0.001) than in other groups (Table 2). There was no significant correlation between FXIa and F1.2 in the ACS group. The $R^2$ for the CAD-MI group was 0.33 (p<0.05).

Example 8

Detection of Elevated FXIa and TF in Samples from Subjects with Cardiovascular Disease Blood samples were collected from subjects confirmed by other diagnostic methods of having suffered from a stroke (acute, or at least three months prior), TIA (acute or at least three months prior), or congestive heart failure; or from subjects that had undergone CABG. Selection and diagnostic criteria are noted above, or are those routinely used for the diagnosis of such conditions. Exclusion criteria are noted above or were similar to those used for exclusion of subjects in the ACS and CAD studies. Blood samples were obtained essentially as described in Example 2 and assayed for the detection of each TF and FXIa. The results are shown in Table 3. Again, no FXIa or TF was detected in the normal, pooled control samples.

As can be seen in the table, an elevation in FXIa was consistently seen in subjects having undergone acute stroke (73%), with a less frequent increase in the less severe ischemic event TIA. Cardiac bypass surgery (CABG) was demonstrated to increase FXIa in 40% of subjects and TF in 20% of the subjects.

Those skilled in the art will recognize, or be able to ascertain using no more than routine experimentation, many equivalents to the specific embodiments of the invention described herein. Such equivalents are intended to be encompassed by the following claims.

All references cited herein are each incorporated by reference as if each were incorporated by reference individually.

TABLE 1

Clinical Parameters for Individuals Included in the Study

|  | Healthy (n = 12) | ACS (n = 26) | CAD (w/ prev MI) n = 29 | CAD (w/o prev MI) n = 24 |
|---|---|---|---|---|
| Age, years | 60 (52-73) | 59 (46-76) | 64 (50-76) | 60 (47-75) |
| Sex, M/F | 9/3 | 21/5 | 21/8 | 14/10 |
| BMI, kg/m2 | 26.2 (22.8-32.3) | 26.5 (21.4-29.8) | 26.4 (22.1-29.8) | 26.5 (21.8-30.6) |
| Current Smokers, n (%) | 4 (33%) | 9 (35%) | 11 (38%) | 5 (21%) |
| Hypertension, n (%) | 0 (0%) | 19 (73%) | 15 (52%) | 14 (58%) |
| Diabetes, n (%) | 0 (0%) | 3 (12%) | 3 (10%) | 3 (12%) |
| Previous MI, n (%) | 0 (0%) | 4 (15%) | 29 (100%) | 0 (0%) |
| POAD, n (%) | 0 (0%) | 0 (0%) | 4 (14%) | 2 (8%) |
| Prev. revascularization, n (%) | 0 (0%) | 3 (11%) | 20 (69%) | 9 (38%) |
| Total cholesterol, mmol/L | 5.41 (4.64-6.76) | 6.20 (3.55-7.72) | 4.41 (3.28-7.81) | 5.1 (2.36-6.99) |
| LDL cholesterol, mmol/L | 3.51 (2.41-4.26) | 3.86 (2.22-5.36) | 2.53 (1.79-5.91) | 2.95 (1.33-4.49) |
| HDL cholesterol, mmol/L | 1.405 (0.90-2.06) | 1.14 (0.67-2.12) | 1.17 (0.65-1.91) | 1.26 (0.57-3.99) |
| Triglycerides, mmol/L | 1.425 (0.72-2.39) | 2.22 (0.49-6.45) | 1.56 (0.7-3.01) | 1.36 (0.42-4.47) |
| Glucose, mmol/L | 5.15 (4.6-6.2) | 6.65 (5.0-16.4)* | 4.9 (3.9-10.5) | 5.55 (4.0-7.7) |
| Creatine, mmol/L | 64.5 (45-93) | 76 (47-128) | 78 (44-119) | 83.5 (57-128)* |
| Troponin, mmol/L | 0 (0-0) | 4.52 (0.01-166.7)* | 0 (0-0) | 0 (0-0) |
| Aspirin, n (%) | 0 (0%) | 26 (100%) | 26 (90%) | 23 (96%) |
| Statins, n (%) | 0 (0%) | 6 (23%) | 25 (86%) | 22 (92%) |

TABLE 1-continued

Clinical Parameters for Individuals Included in the Study

|  | Healthy (n = 12) | ACS (n = 26) | CAD (w/ prev MI) n = 29 | CAD (w/o prev MI) n = 24 |
|---|---|---|---|---|
| β-blockers, n (%) | 0 (0%) | 11 (42%) | 20 (69%) | 21 (88%) |
| ACE inhibitors, n (%) | 0 (0%) | 9 (35%) | 19 (66%) | 15 (62%) |
| Calcium antagonists, n (%) | 0 (0%) | 3 (12%) | 4 (14%) | 6 (25%) |
| Diuretics, n (%) | 0 (0%) | 3 (12%) | 6 (21%) | 6 (25%) |
| APTT, sec | 30.8 (27.8-34.2) | 29.1 (21.0-49.0) | 33.5 (27.6-40.6) | 32.4 (25.6-40.5) |
| Platelets, $10^3$/uL | 263 (189-310) | 240 (131-341) | 264 (189-403) | 242 (83-413) |
| Fibrinogen, g/L | 2.82 (2.14-3.36) | 3.72 (2.57-5.85)* | 3.81 (1.96-5.7) | 3.20 (2.22-7.23) |
| CRP, mg/L | 1.72 (0.88-2.31) | 3.035 (0.5-34.81)* | 1.9 (0.5-9.75) | 2.01 (0.42-6.12) |

*p < 0.05 when compared to healthy

TABLE 2

Levels of IL-6, TAT, F1.2, FXIa and TF Activity, and their Correlations

|  | ACS | Stable CAD w/Prev. MI | Stable CAD No Prev. MI | Healthy |
|---|---|---|---|---|
| N | 26 | 29 | 24 | 12 |
| FXIa (n) | 25 | 22 | 5 | 0 |
| FXIa (pM) | 50.3 ± 32.8 | 41.7 ± 45.4 | 8.1 ± 19.9 | 0 |
|  | 10 | 2 | 1 | 0 |
|  | <0.4 | <0.4 | <0.4 | 0 |
| IL-6 (pg/mL) | 3.46 ± 1.19 | 1.83 ± 0.60 | 1.64 ± 0.76 | 1.25 ± 0.25 |
| TAT (ng/mL) | 6.75 ± 1.44 | 2.88 ± 0.58 | 2.76 ± 0.61 | 2.48 ± 0.19 |
| F1.2 | 1.40 ± 0.59 | 0.85 ± 0.33 | 0.73 ± 022 | 0.72 ± 0.13 |
| R-Sq (XIa/IL-6) | 0.385 | 0.594 | ND | ND |
| R-Sq (XIa/TAT) | 0.628 | 0.637 | ND | ND |
| R-Sq (XIa/F1.2) | 0.006 | 0.324 | ND | ND |

TABLE 3

Frequency of factor XIa and tissue factor activity in patients with cardiovascular diseases

| Diagnosis | N = | TF n/N (%) | FXIa n/N (%) |
|---|---|---|---|
| Acute Coronary Syndrome (ACS) | 26 | 10/26 (38) | 25/26 (96) |
| Stable Coronary Artery Disease | 53 | 3/53 (6) | 27/53 (51) |
| With previous myocardial infarction | 29 | 2/29 (7) | 22/29 (76) |
| Without previous myocardial infarction | 24 | 1/24 (4) | 5/24 (21) |
| Coronary Artery Bypass Graft (CABG) | 122 | 25/122 (20) | 49/122 (40) |
| Heart Failure | 53 | 20/53 (38) | 22/53 (42) |
| Aortic Stenosis | 53 | 14/53 (26) | 12/53 (23) |
| Stroke | 471 | 87/466 (19) | 106/145 (73) |
| Previous stroke | 165 | 20/164 (12) | 57/165 (35) |
| Acute stroke | 148 | 48/142 (34) | 106/145 (73) |
| Previous transient ischemic attack | 79 | 4/79 (5) | 9/79 (11) |
| Acute transient ischemic attack | 79 | 15/79 (19) | 39/79 (49) |

We claim:

1. A method of detecting Factor XIa (FXIa) in a test sample from a subject suffering from or suspected of suffering from at least one of inflammation, acute coronary syndrome (ACS), myocardial infarction, coronary artery disease (CAD), heart failure, aortic stenosis, stroke, or transient ischemic attack comprising:
   a) contacting the test sample with a contact pathway coagulation inhibitor that does not inhibit FXIa;
   b) contacting a portion of the contact pathway coagulation inhibited test sample with a FXIa specific antibody under conditions to permit binding of the antibody to FXIa;
   c) contacting the antibody treated test sample with $Ca^{++}$ and a phospholipid surface;
   d) detecting clotting time of the antibody treated test sample relative a reference portion of the contact pathway coagulation inhibited test sample not contacted with antibody; and
   e) correlating a prolongation of clotting time of the antibody treated portion of the test sample relative to the reference portion of the sample with inflammation, acute coronary syndrome (ACS), myocardial infarction, coronary artery disease (CAD), heart failure, aortic stenosis, stroke, or transient ischemic attack in the subject.

2. A method of detecting Factor XIa (FXIa) in a test sample from a subject suffering from or suspected of suffering from at least one of inflammation, acute coronary syndrome (ACS), myocardial infarction, coronary artery disease (CAD), heart failure, aortic stenosis, stroke, or transient ischemic attack comprising:
   a) contacting a portion of the test sample with a FXIa specific antibody; and
   b) detecting clotting time in the antibody treated test sample portion relative a reference portion of the test sample not contacted with antibody; and
   c) correlating a prolongation of clotting time of the antibody treated portion of the test sample relative to the reference portion of the sample with inflammation, acute coronary syndrome (ACS), myocardial infarction, coronary artery disease (CAD), heart failure, aortic stenosis, stroke, or transient ischemic attack in the subject.

3. The method of claim 1, wherein the test sample is contacted with a calcium chelator.

4. The method of claim 2, further comprising determining the clotting time of a sample is from a normal subject not treated with a FXIa antibody is determined.

* * * * *